United States Patent
Hart et al.

(10) Patent No.: US 11,813,023 B2
(45) Date of Patent: Nov. 14, 2023

(54) FUNDUS IMAGE CAPTURING

(71) Applicant: Welch Allyn, Inc., Skaneateles Falls, NY (US)

(72) Inventors: Allen R. Hart, Knoxville, TN (US); Christian H. Reinke, York, SC (US); Carlos Suarez, Syracuse, NY (US); Ynjiun P. Wang, Cupertino, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 236 days.

(21) Appl. No.: 17/220,005

(22) Filed: Apr. 1, 2021

(65) Prior Publication Data

US 2021/0212562 A1     Jul. 15, 2021

Related U.S. Application Data

(63) Continuation of application No. 16/229,939, filed on Dec. 21, 2018, now Pat. No. 10,993,613.

(51) Int. Cl.
| | |
|---|---|
| *A61B 3/12* | (2006.01) |
| *A61B 3/14* | (2006.01) |
| *A61B 3/15* | (2006.01) |
| *A61B 3/00* | (2006.01) |

(52) U.S. Cl.
CPC .............. *A61B 3/12* (2013.01); *A61B 3/0025* (2013.01); *A61B 3/0041* (2013.01); *A61B 3/0058* (2013.01); *A61B 3/0075* (2013.01); *A61B 3/14* (2013.01); *A61B 3/152* (2013.01); *A61B 3/154* (2013.01)

(58) Field of Classification Search
CPC .. A61B 3/12; A61B 3/15; A61B 3/152; A61B 3/154
See application file for complete search history.

(56) References Cited

U.S. PATENT DOCUMENTS

| | | | |
|---|---|---|---|
| 5,614,967 A | 3/1997 | Ishikawa et al. | |
| 6,309,068 B1 * | 10/2001 | Kohayakawa | A61B 3/028 351/221 |
| 6,666,855 B2 | 12/2003 | Somani et al. | |
| 7,456,949 B2 | 11/2008 | Somani et al. | |
| 7,798,643 B2 | 9/2010 | Waldorf et al. | |
| 8,246,610 B2 | 8/2012 | Riedel et al. | |

(Continued)

FOREIGN PATENT DOCUMENTS

| | | |
|---|---|---|
| EP | 2 926 722 A1 | 7/2015 |
| WO | 2018/049041 A1 | 3/2018 |

OTHER PUBLICATIONS

Extended European Search Report for Application No. 19216686.6 dated May 4, 2020.

(Continued)

*Primary Examiner* — Cara E Rakowski
(74) *Attorney, Agent, or Firm* — Merchant & Gould P.C.

(57) ABSTRACT

An example device is configured to capture an image of an eye. The device includes a camera configured to capture the image of the eye. The device also includes: a first base configured to be moved along a first axis to position the camera to capture the image of the eye; a second base configured to be moved along a second axis to position the camera to capture the image of the eye; and a third base configured to be moved along a third axis to position the camera to capture the image of the eye.

19 Claims, 25 Drawing Sheets

(56) References Cited

U.S. PATENT DOCUMENTS

| | | |
|---|---|---|
| 8,807,751 B2 | 8/2014 | Kahn et al. |
| 8,939,583 B2 | 1/2015 | Borycki et al. |
| 10,136,804 B2 | 11/2018 | Wang et al. |
| 2009/0153796 A1 | 6/2009 | Rabner |
| 2012/0220850 A1 | 8/2012 | Umekawa |
| 2013/0162950 A1 | 6/2013 | Umekawa |
| 2013/0250243 A1* | 9/2013 | Cech ................. A61B 3/12 351/208 |
| 2013/0271727 A1 | 10/2013 | Akiba |
| 2014/0313485 A1 | 10/2014 | Umekawa |
| 2015/0272436 A1 | 10/2015 | Hayashi |
| 2016/0106316 A1 | 4/2016 | Tachikawa |
| 2016/0338589 A1 | 11/2016 | Carrasco-Zevallos et al. |
| 2017/0020389 A1* | 1/2017 | Wang ............. A61B 3/0025 |
| 2017/0071466 A1* | 3/2017 | Kowal ............ A61B 3/0075 |
| 2017/0119241 A1 | 5/2017 | Farchione |
| 2017/0156591 A1 | 6/2017 | Berestka et al. |
| 2018/0084995 A1 | 3/2018 | Wang |
| 2018/0263488 A1* | 9/2018 | Pamplona ........ A61B 3/0041 |
| 2018/0336679 A1 | 11/2018 | Farchione et al. |

OTHER PUBLICATIONS

Examination Report No. 1 for standard patent application for Australian Application No. 2019283798 dated Jun. 17, 2020.

* cited by examiner

FUNDUS IMAGE CAPTURING

RELATED APPLICATION(S)

This patent application is related to U.S. patent application Ser. No. 15/054,558 filed on Feb. 26, 2016, the entirety of which is hereby incorporated by reference.

INTRODUCTION

Diabetic retinopathy and other similar disease states can be diagnosed by studying an image of the retina. Retinal images can be reviewed manually by a clinician. However, manual review is labor-intensive process and subject to error.

For example, people with type 1 or type 2 diabetes can develop eye disease as a result of having diabetes. One of the most common diabetic eye diseases is diabetic retinopathy, which is damage to the blood vessels of the light-sensitive tissue at the back of the eye, known as the retina. Trained medical professionals use cameras during eye examinations for diabetic retinopathy screening. The cameras can produce images of the back of the eye, and trained medical professionals use those images to diagnose and treat diabetic retinopathy.

SUMMARY

In one aspect, an example device is configured to capture an image of an eye. The device includes a camera configured to capture the image of the eye. The device also includes: a first base configured to be moved along a first axis to position the camera to capture the image of the eye; a second base configured to be moved along a second axis to position the camera to capture the image of the eye; and a third base configured to be moved along a third axis to position the camera to capture the image of the eye.

DESCRIPTION OF THE FIGURES

The following drawing figures, which form a part of this application, are illustrative of described technology and are not meant to limit the scope of the disclosure in any manner.

DETAILED DESCRIPTION

Figure 1:
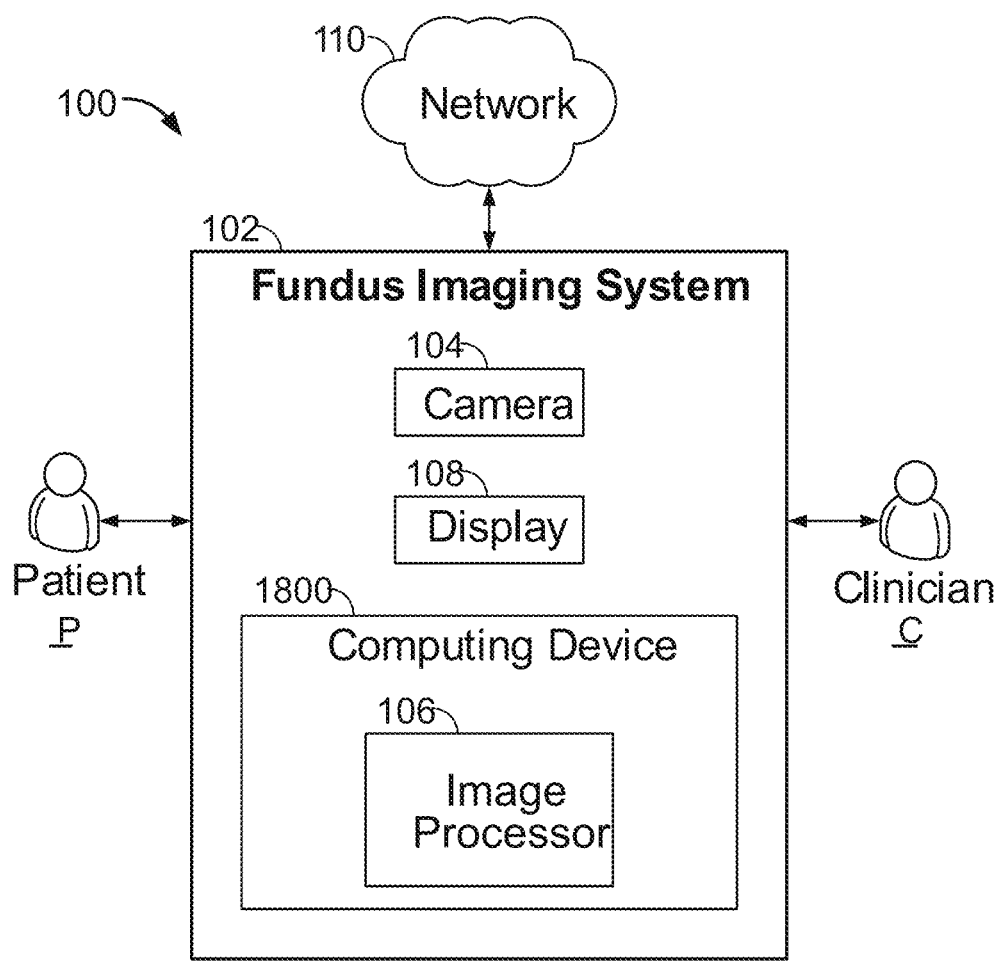
FIG. 1 is an embodiment of an example system for capturing images of a patient's fundus.
Figure 2:
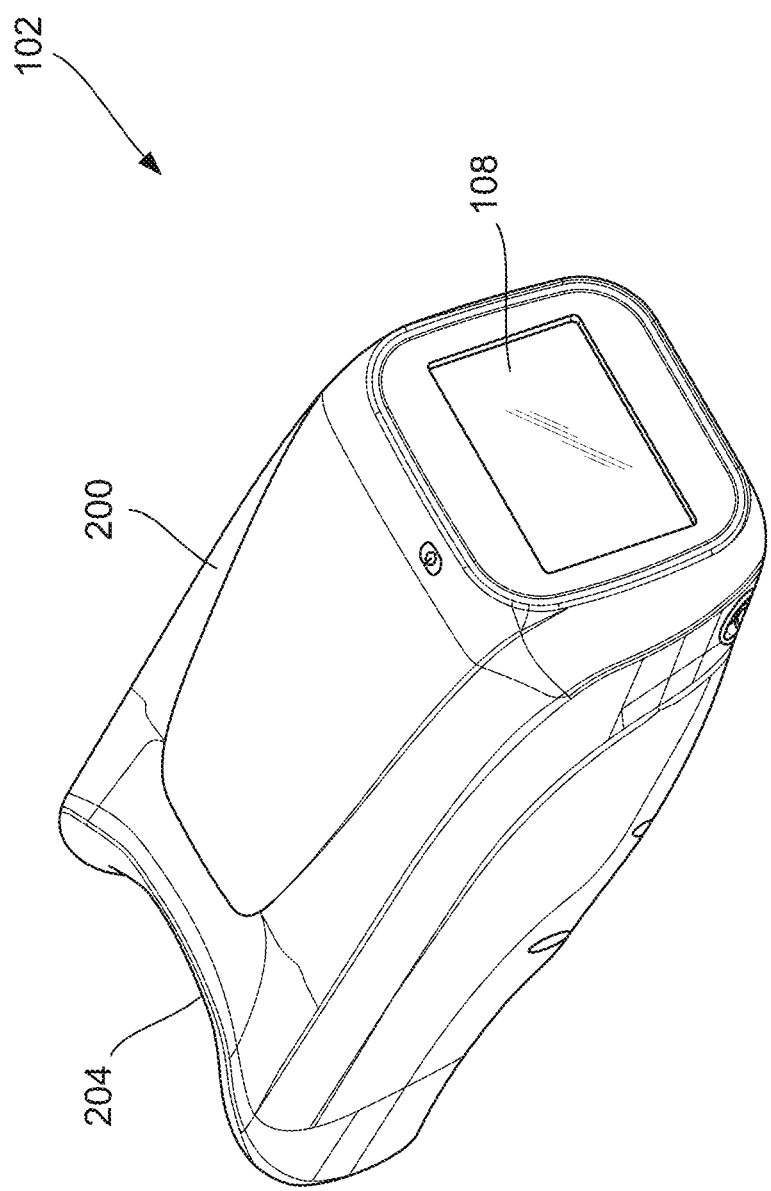
FIG. 2 is an embodiment of an example fundus imaging system of FIG. 1.
Figure 3:
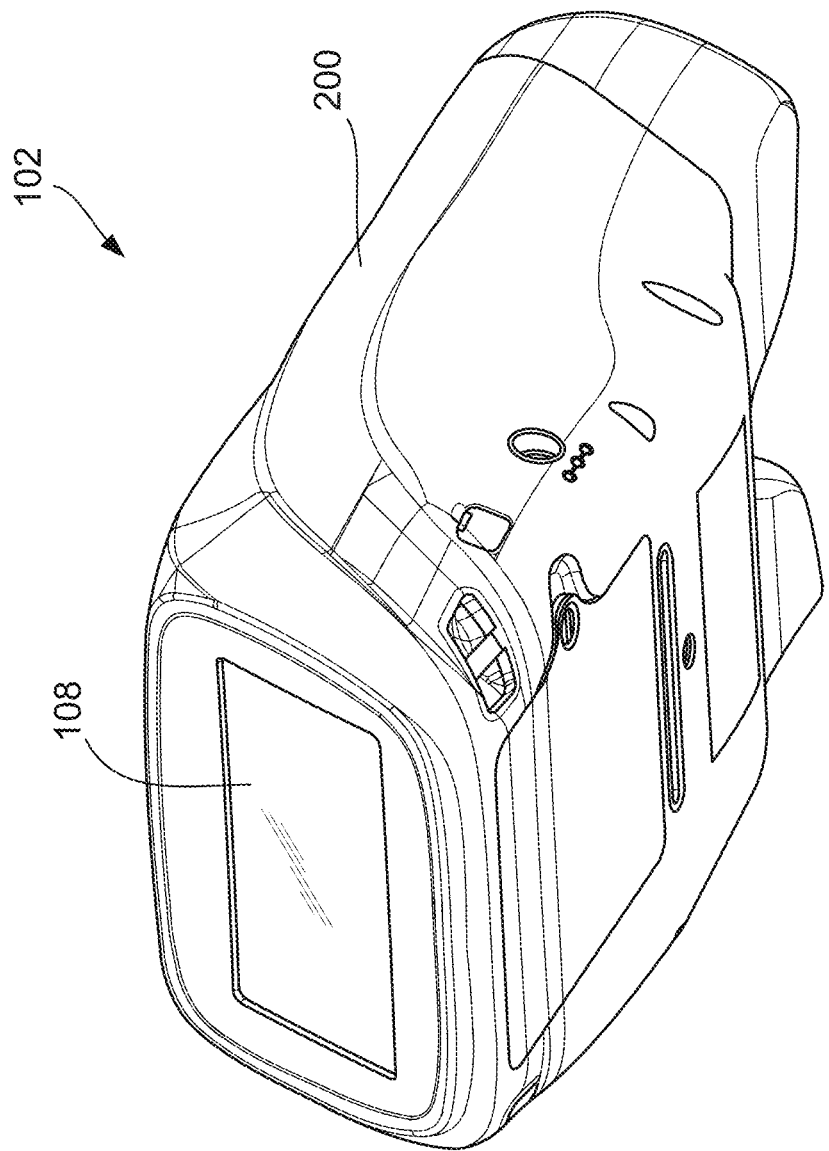
FIG. 3 is another view of the example fundus imaging system of FIG. 2.

FIG. 1 is a schematic block diagram illustrating an example system 100 for recording and viewing an image of a patient's fundus. In this example, the system 100 includes a patient P, a fundus imaging system 102, a computing device 1800 including an image processor 106, a camera 104 in communication with the computing device 1800, a display 108 in communication with the computing device 1800 and used by clinician C, and a network 110. An embodiment of the example fundus imaging system 102 is shown and described in more detail below with reference to FIG. 2-25.

The fundus imaging system 102 functions to create a set of digital images of a patient's P eye fundus. As used herein, "fundus" refers to the eye fundus and includes the retina, optic nerve, macula, vitreous, choroid and posterior pole.

In this example, one or more images of the eye are desired. For instance, the patient P is being screened for an eye disease, such as diabetic retinopathy. The fundus imaging system 102 can also be used to provide images of the eye for other purposes, such as to diagnose or monitor the progression of a disease such as diabetic retinopathy.

The fundus imaging system 102 includes a handheld housing that supports the system's components. The housing supports one or two apertures for imaging one or two eyes at a time. In embodiments, the housing supports positional guides for the patient P, such as an optional adjustable chin rest. The positional guide or guides help to align the patient's P eye or eyes with the one or two apertures. In embodiments, the housing supports means for raising and lowering the one or more apertures to align them with the patient's P eye or eyes. Once the patient's P eyes are aligned, the clinician C then initiates the image captures by the fundus imaging system 102.

One technique for fundus imaging requires mydriasis, or the dilation of the patient's pupil, which can be painful and/or inconvenient to the patient P. Example system 100 does not require a mydriatic drug to be administered to the patient P before imaging, although the system 100 can image the fundus if a mydriatic drug has been administered.

The system 100 can be used to assist the clinician C in screening for, monitoring, or diagnosing various eye diseases, such as hypertension, diabetic retinopathy, glaucoma and papilledema. The clinician C that operates the fundus imaging system 102 can be different from the clinician C evaluating the resulting image.

In the example embodiment 100, the fundus imaging system 102 includes a camera 104 in communication with an image processor 106. In this embodiment, the camera 104 is a digital camera including a lens, an aperture, and a sensor array. The camera 104 lens is a variable focus lens, such as a lens moved by a step motor, or a fluid lens, also known as a liquid lens in the art. The camera 104 is configured to record images of the fundus one eye at a time. In other embodiments, the camera 104 is configured to record an image of both eyes substantially simultaneously. In those embodiments, the fundus imaging system 102 can include two separate cameras, one for each eye.

In example system 100, the image processor 106 is operatively coupled to the camera 104 and configured to communicate with the network 110 and display 108.

The image processor 106 regulates the operation of the camera 104. Components of an example computing device, including an image processor, are shown in more detail in FIG. 25, which is described further below.

The display 108 is in communication with the image processor 106. In the example embodiment, the housing supports the display 108. In other embodiments, the display connects to the image processor, such as a smart phone, tablet computer, or external monitor. The display 108 functions to reproduce the images produced by the fundus imaging system 102 in a size and format readable by the clinician C. For example, the display 108 can be a liquid crystal display (LCD) and active matrix organic light emitting diode (AMOLED) display. The display can be touch sensitive.

The example fundus imaging system 102 is connected to a network 110. The network 110 may include any type of wireless network, a wired network, or any communication network known in the art. For example, wireless connections can include cellular network connections and connections made using protocols such as 802.11a, b, and/or g. In other examples, a wireless connection can be accomplished directly between the fundus imaging system 102 and an external display using one or more wired or wireless protocols, such as Bluetooth, Wi-Fi Direct, radio-frequency identification (RFID), or Zigbee. Other configurations are possible.

Referring now to FIGS. 2-12, the fundus imaging system 102 is shown. The fundus imaging system 102 includes a housing 200 that supports a display 108 at a first end and an opposite end 204 configured to engage one or both eyes of the patient P. As described herein, the fundus imaging system 102 can be used to implement one or more of the described methods for imaging of the fundus.

The housing 200 of example fundus imaging system 102 is sized to be handheld. The display 108 can display images of the eye and controls for capturing those images. In some embodiment, the display 108 can be a touchscreen. In embodiments, the housing 200 additionally supports one or more user input buttons near display 108. The display 108 can be used to initiate the image capture sequence, as described herein. Thus, the fundus imaging system 102 is capable of being configured such that the clinician C can implement one or more automatic and/or manual workflows for the capture of images of the patient P's eyes.

Figure 4:
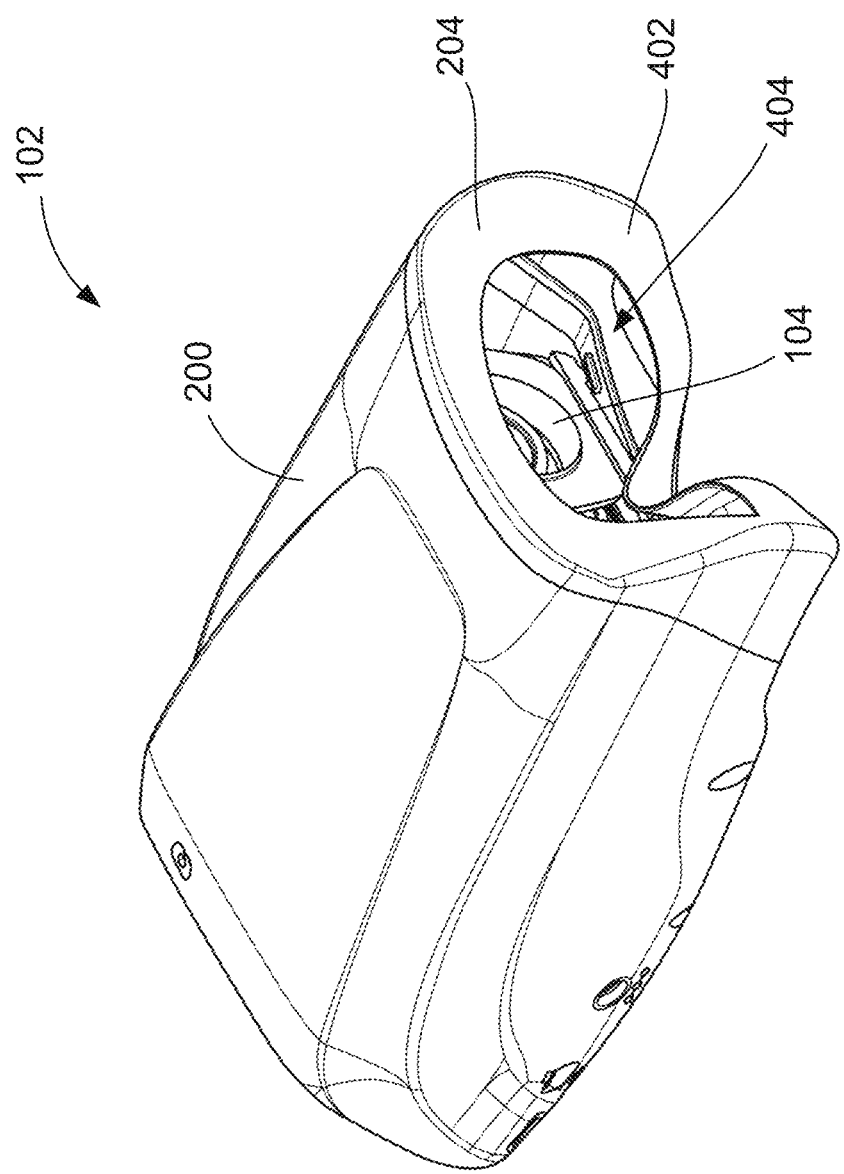
FIG. 4 is another view of the example fundus imaging system of FIG. 2.
Figure 5:
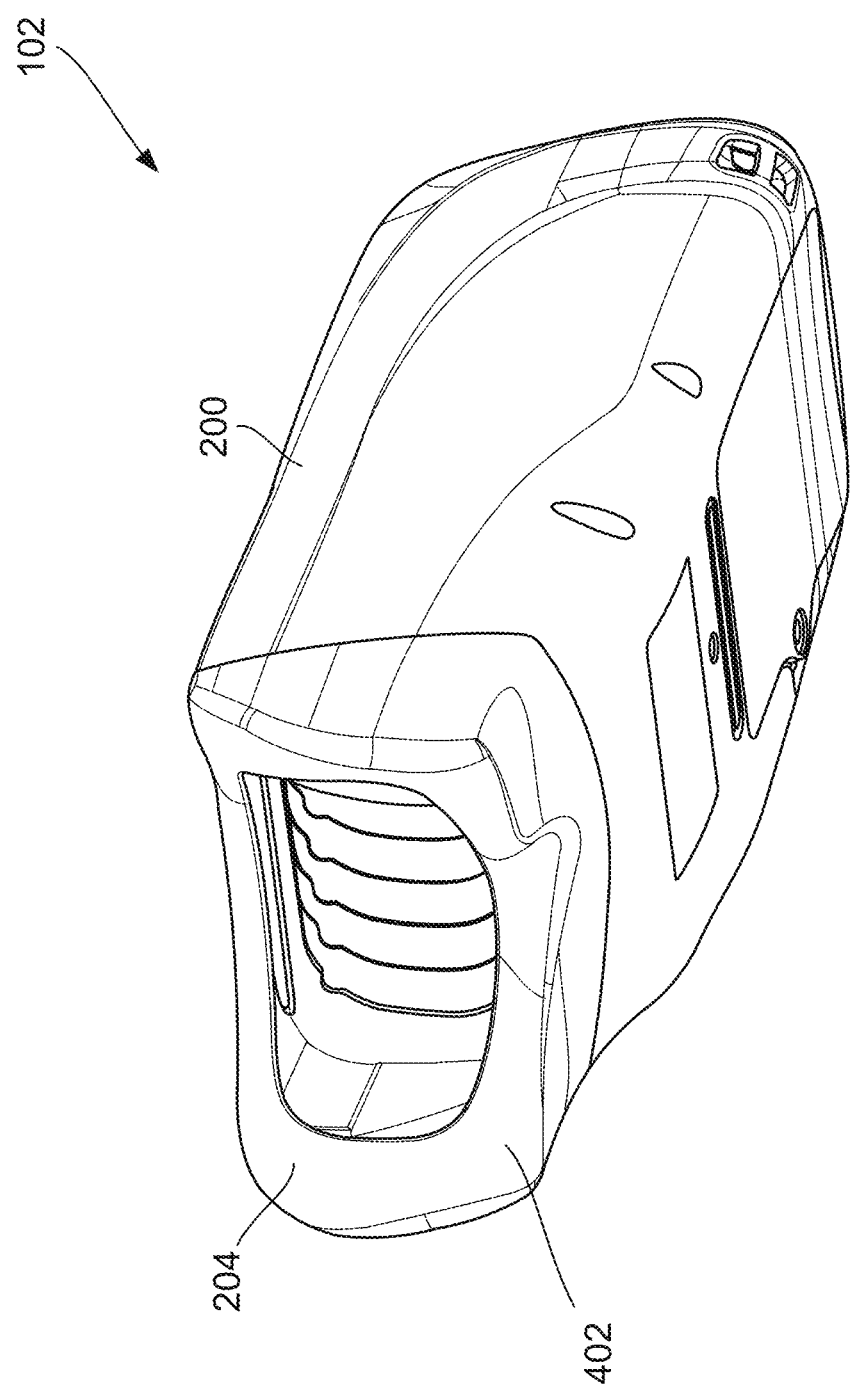
FIG. 5 is another view of the example fundus imaging system of FIG. 2.
Figure 6:
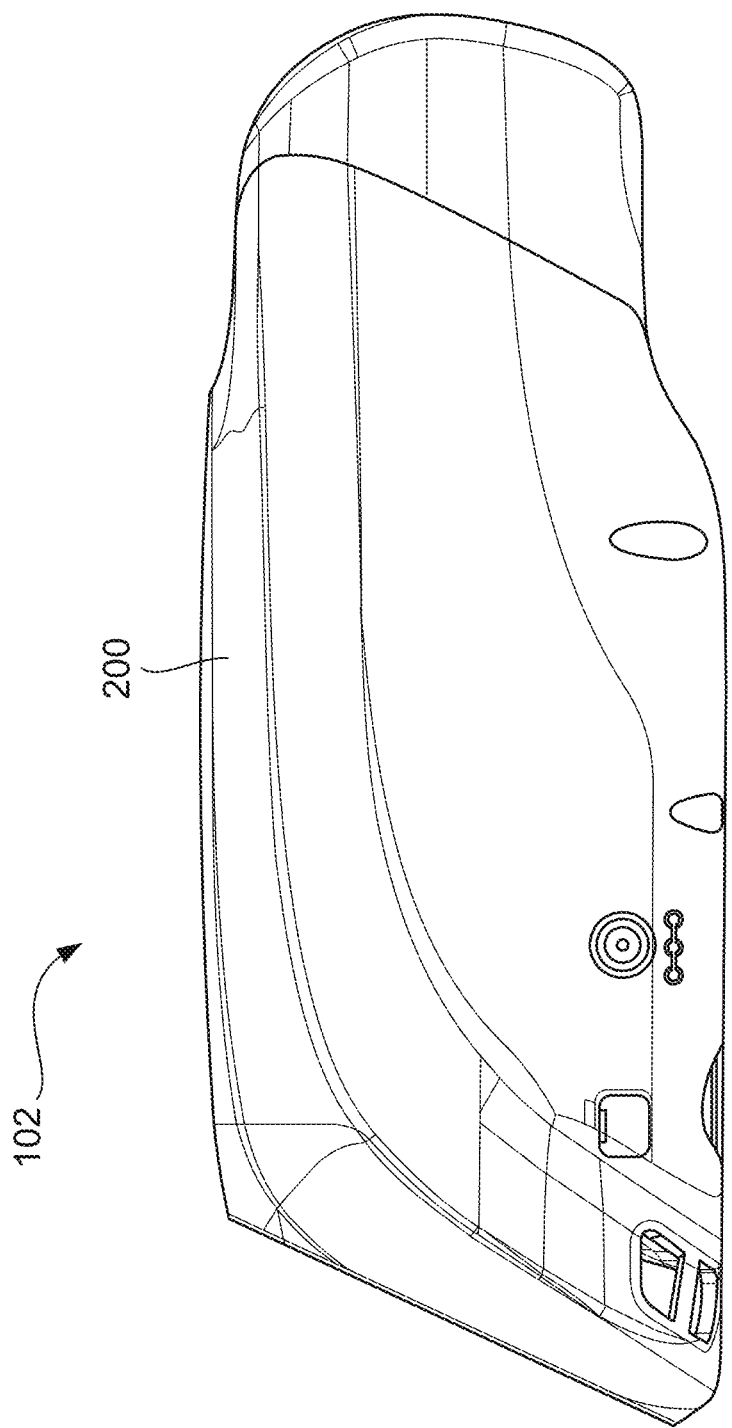
FIG. 6 is another view of the example fundus imaging system of FIG. 2.
Figure 7:
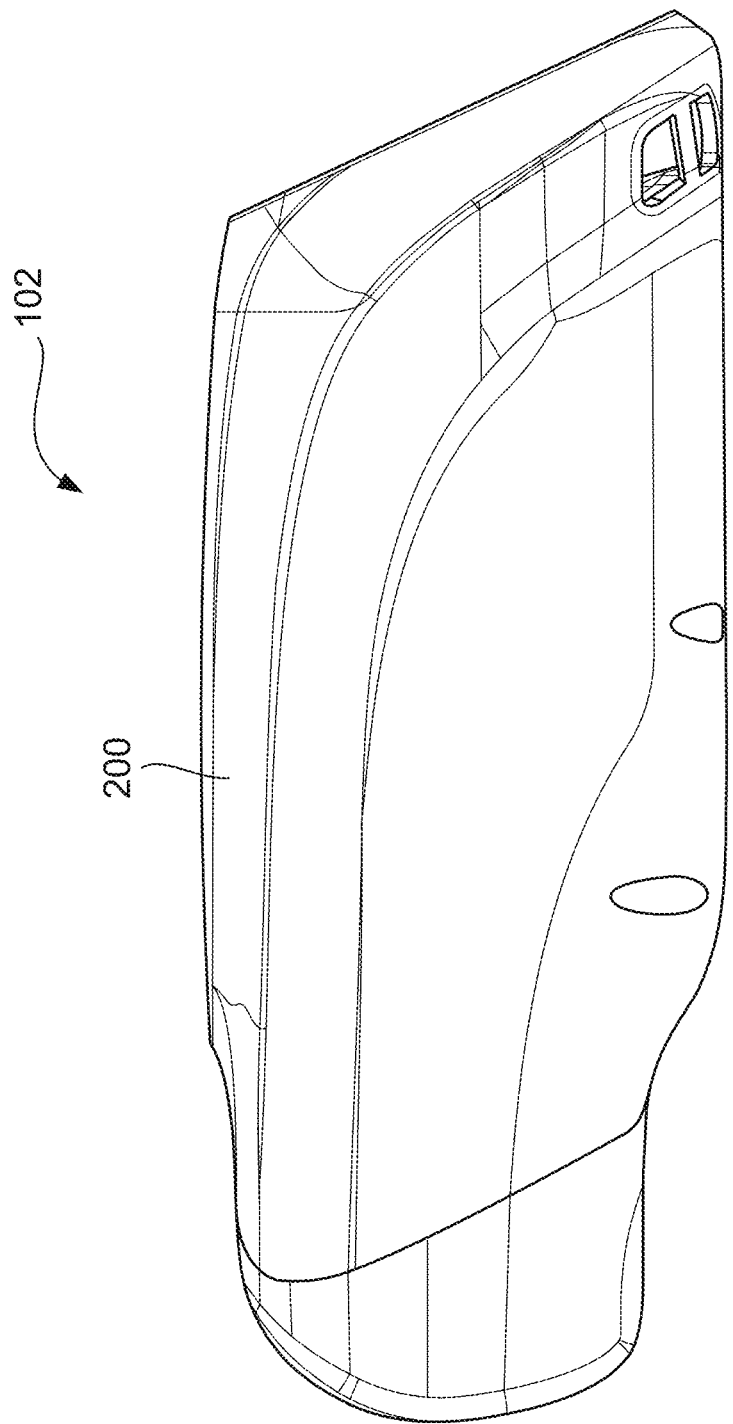
FIG. 7 is another view of the example fundus imaging system of FIG. 2.
Figure 8:
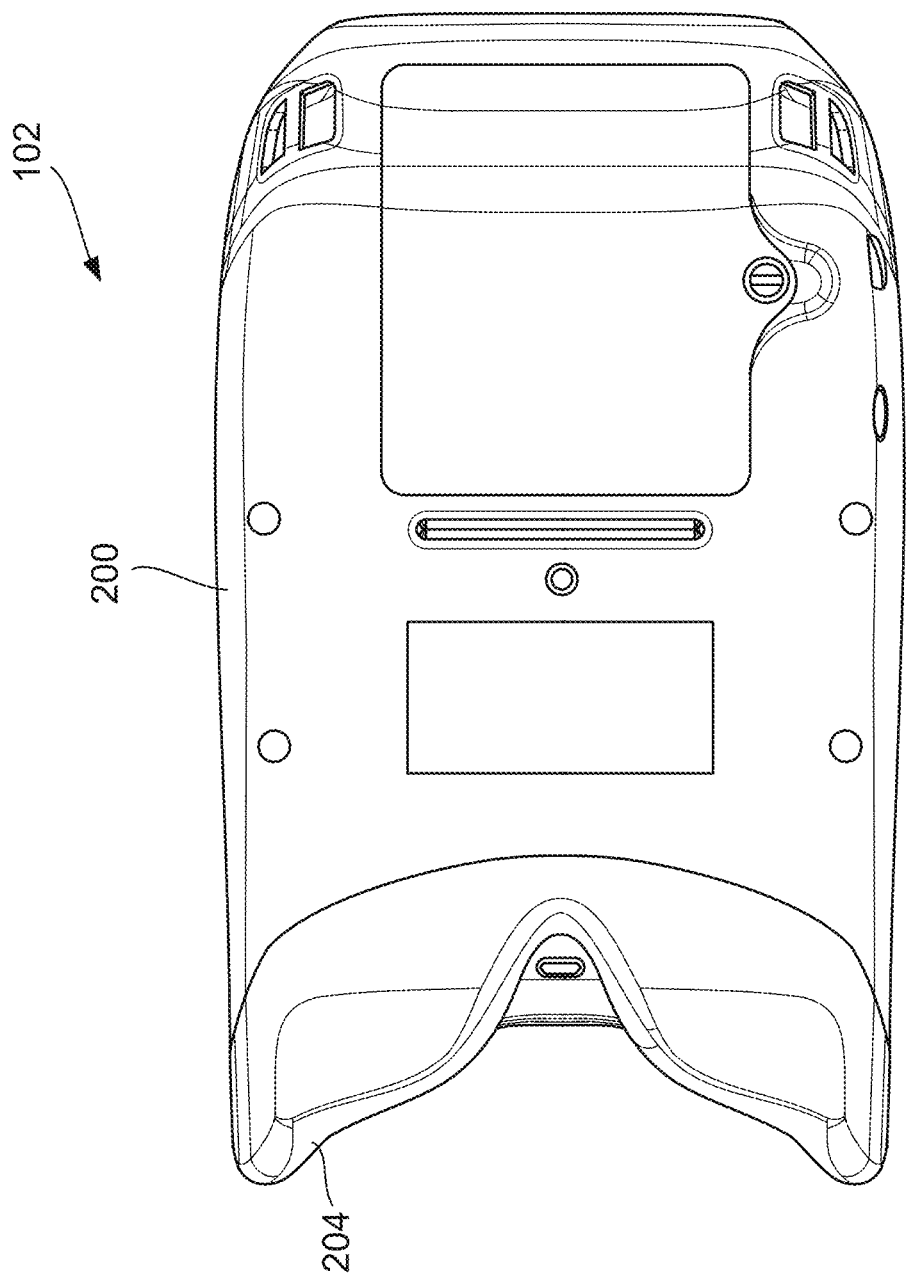
FIG. 8 is another view of the example fundus imaging system of FIG. 2.
Figure 9:
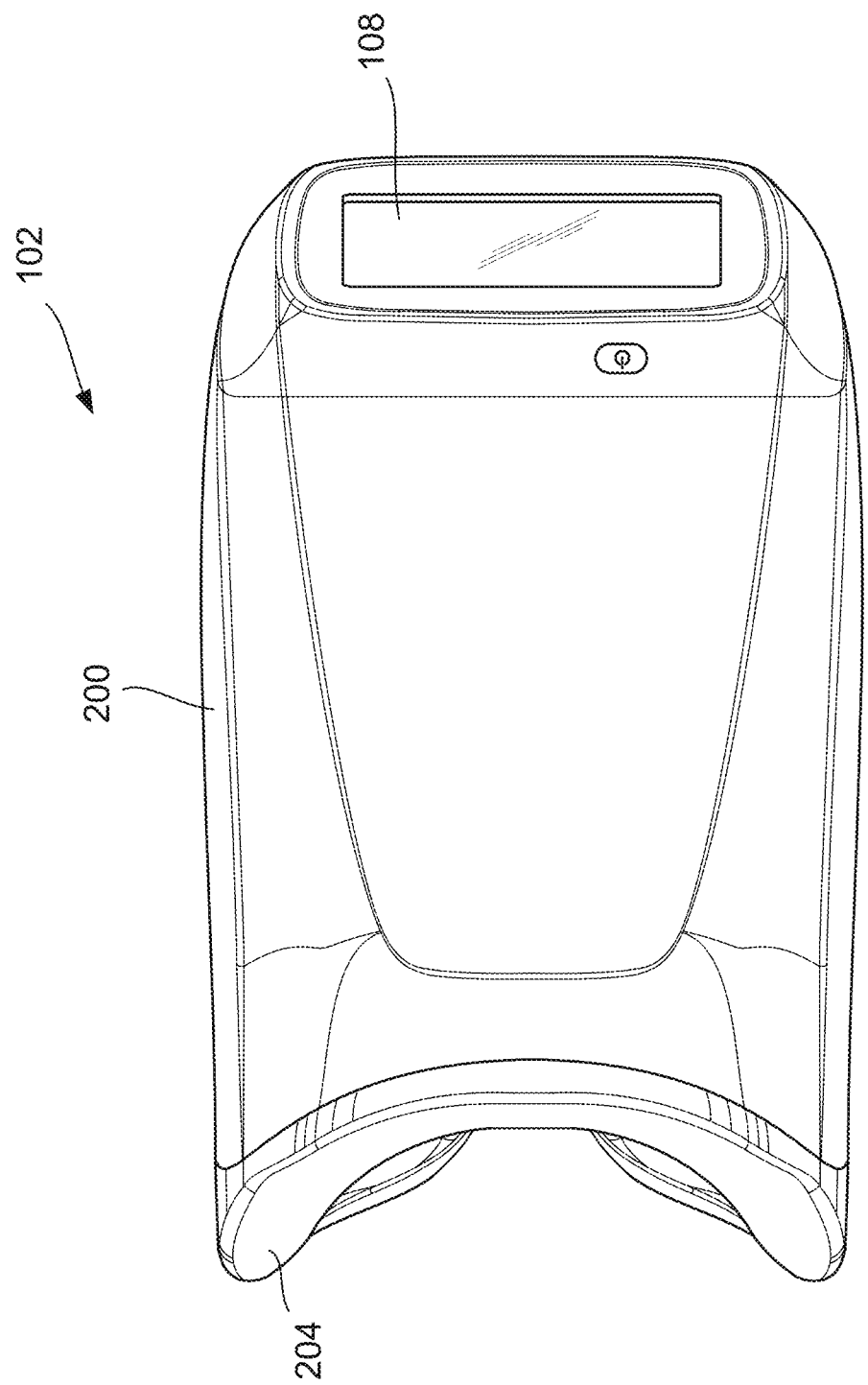
FIG. 9 is another view of the example fundus imaging system of FIG. 2.
Figure 10:
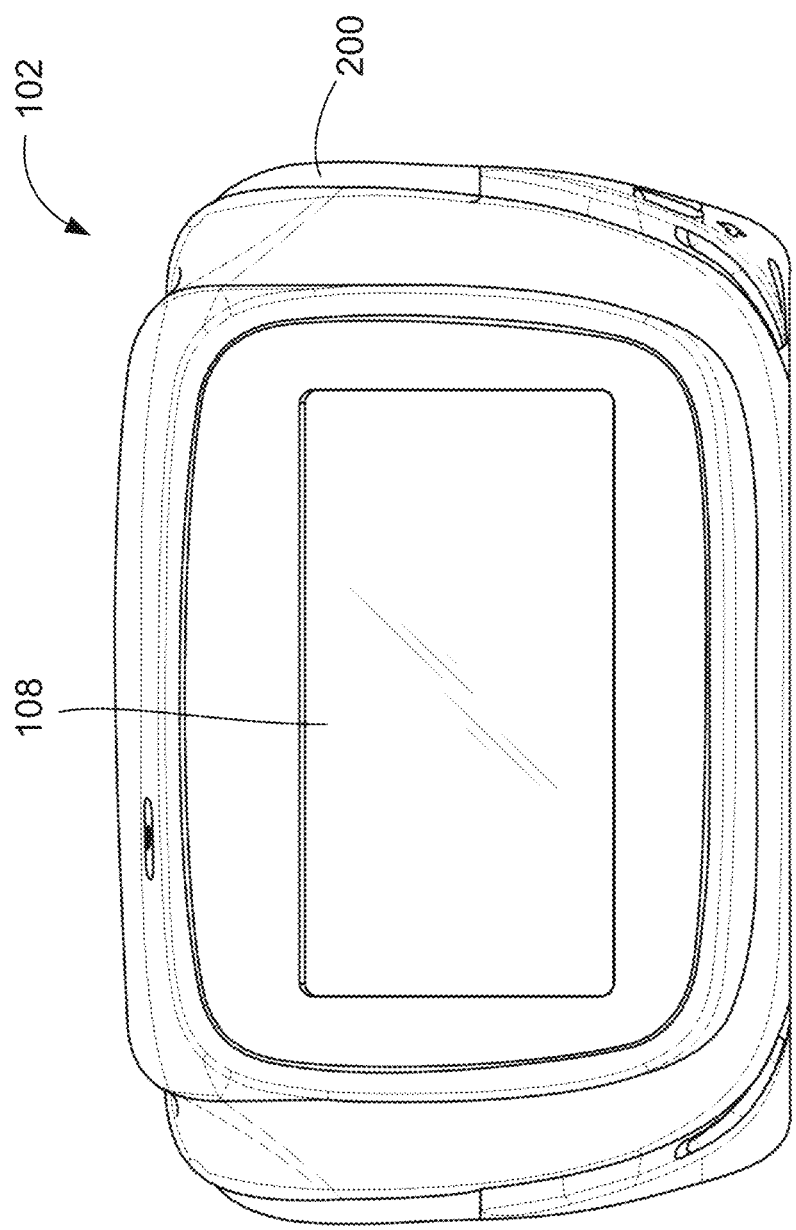
FIG. 10 is another view of the example fundus imaging system of FIG. 2.
Figure 11:
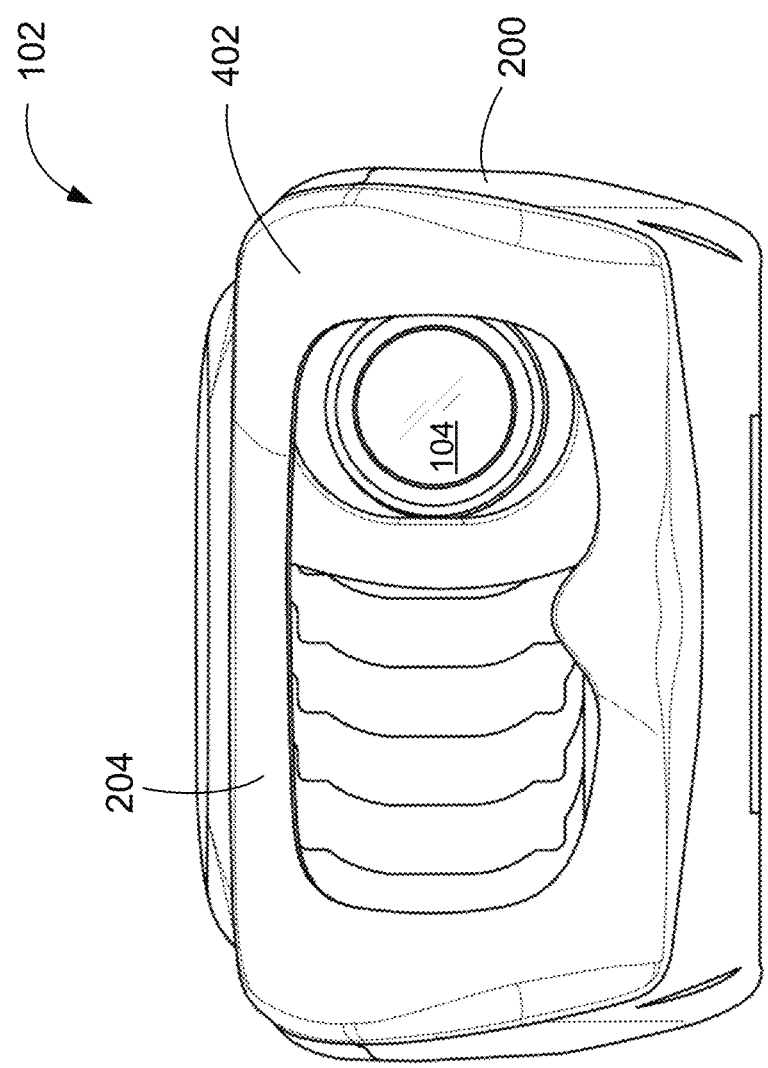
FIG. 11 is another view of the example fundus imaging system of FIG. 2.
Figure 12:
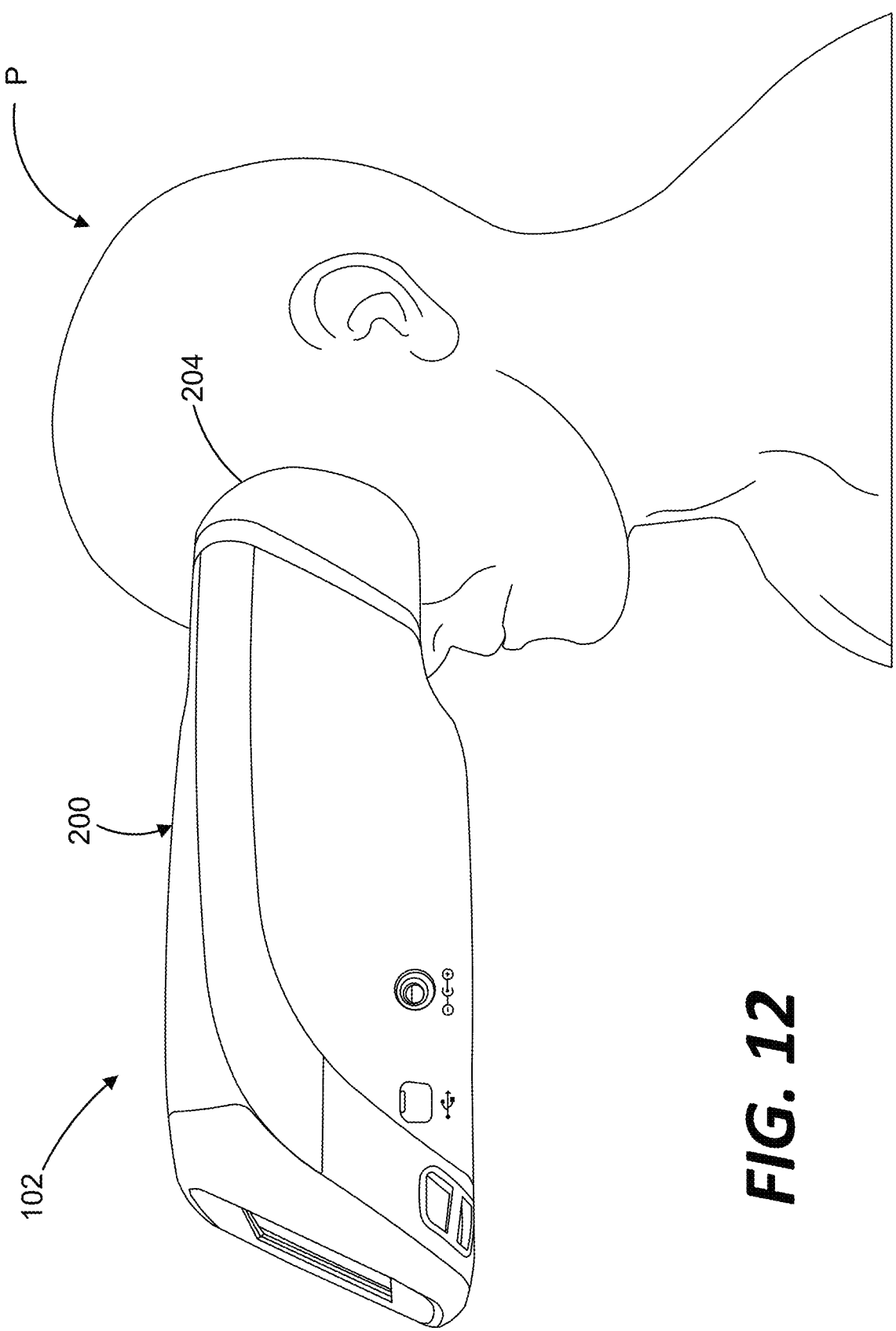
FIG. 12 is another view of the example fundus imaging system of FIG. 2 positioned against a patient's head.
Figure 13:
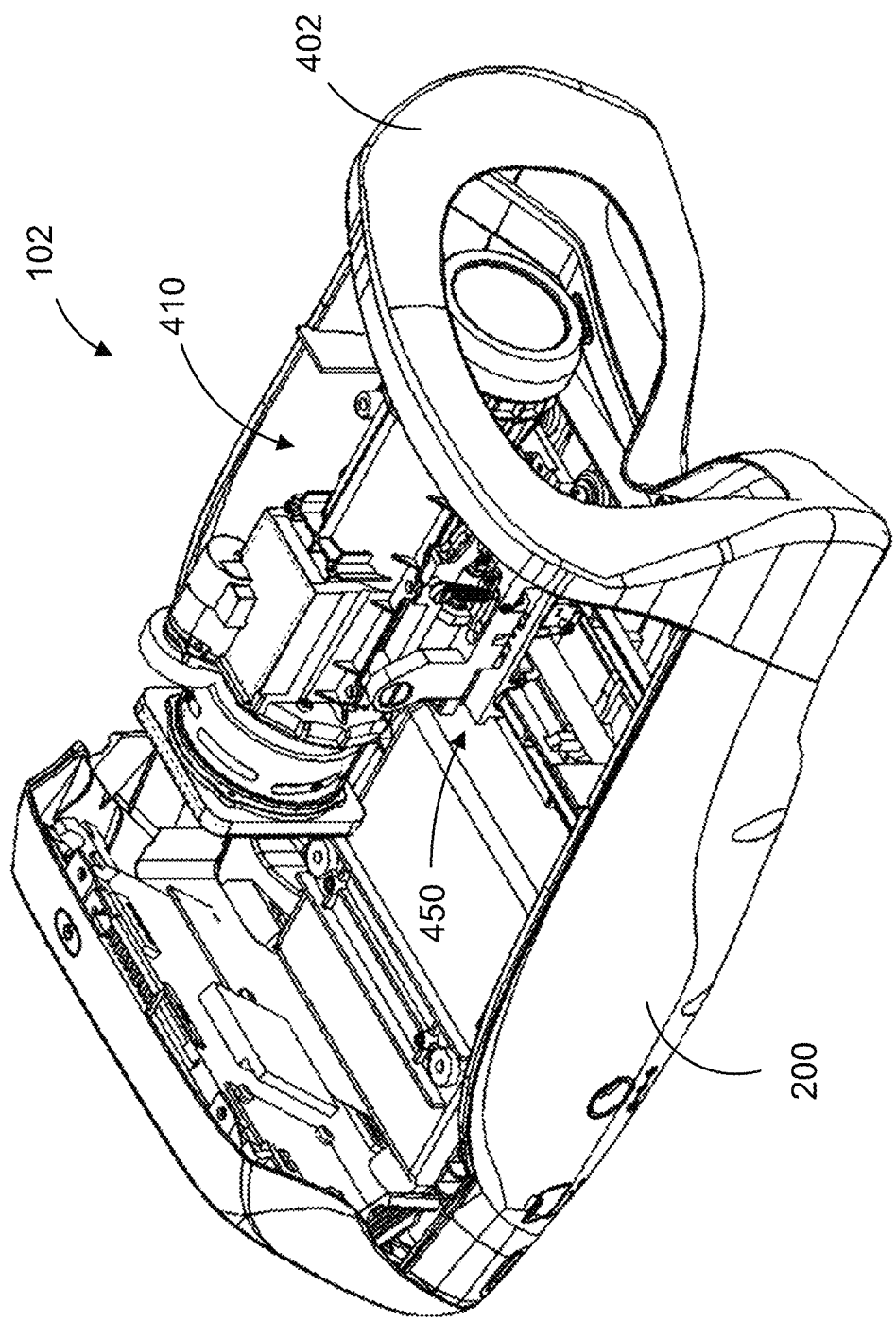
FIG. 13 is another view of the example fundus imaging system of FIG. 2 with a portion of the housing removed.
Figure 14:
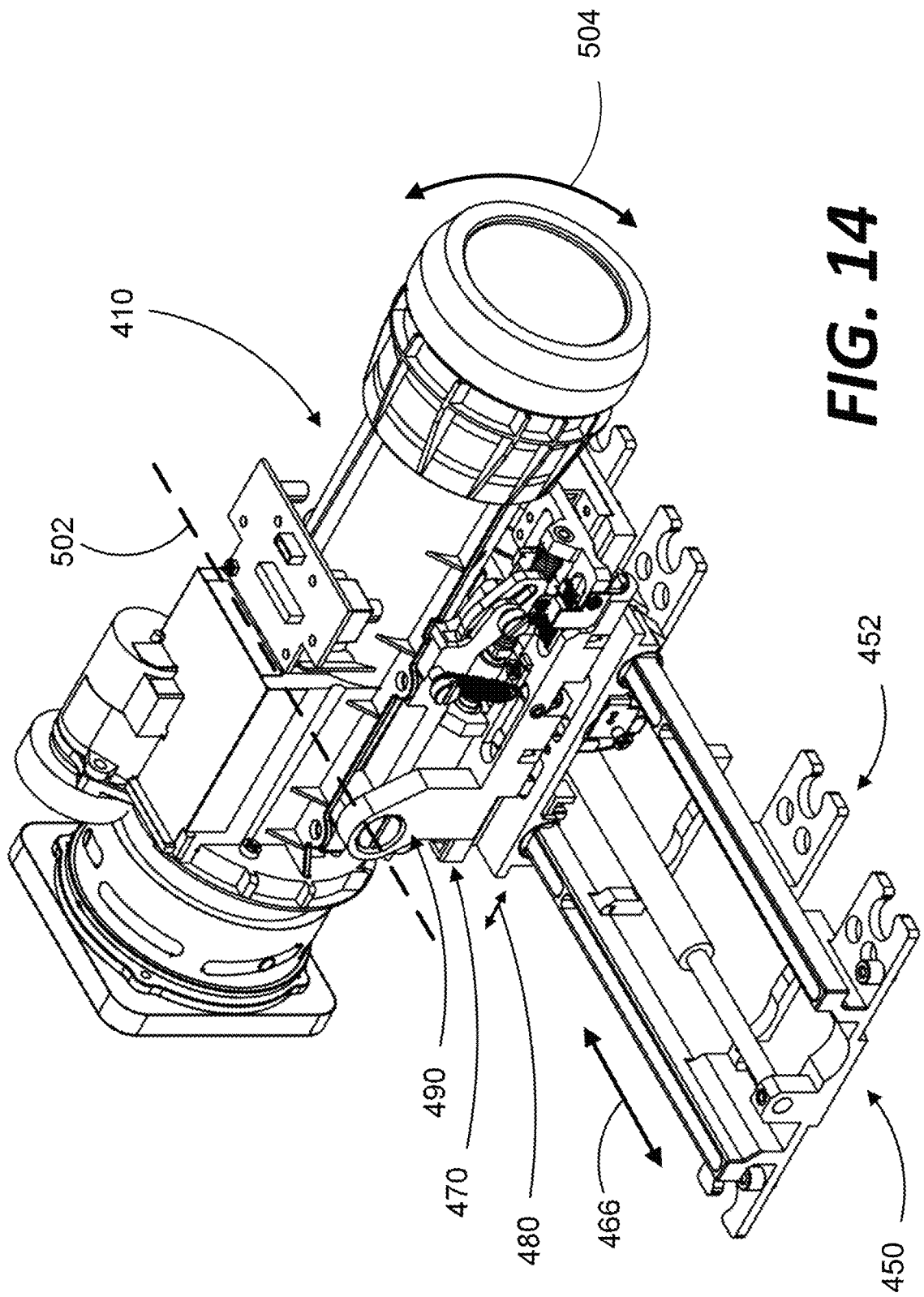
FIG. 14 is an embodiment of an example optical lens module of the fundus imaging system of FIG. 2.

As shown in FIGS. 4 and 11, the opposite end 204 of the housing 200 includes a surface 402 configured to engage the patient P's head. Specifically, the surface 402 is configured to be positioned again the patient P's head and to surround both eyes of the patient P. See FIG. 12. The camera 104 of the fundus imaging system 102 is positioned within a cavity 404 formed at the end 204 of the housing 200. As described further below, the camera 104 is configured to be moved in at least three directions to accomplish imaging of the fundus of both eyes of the patient P as the housing 200 of the fundus imaging system 102 is held positioned against the patient P's head.

FIGS. 13-22 illustrates internal components of the fundus imaging system 102. As depicted, the fundus imaging system 102 includes an optical lens module 410 that is moved along multiple axes by a base assembly 450.

Figure 15:
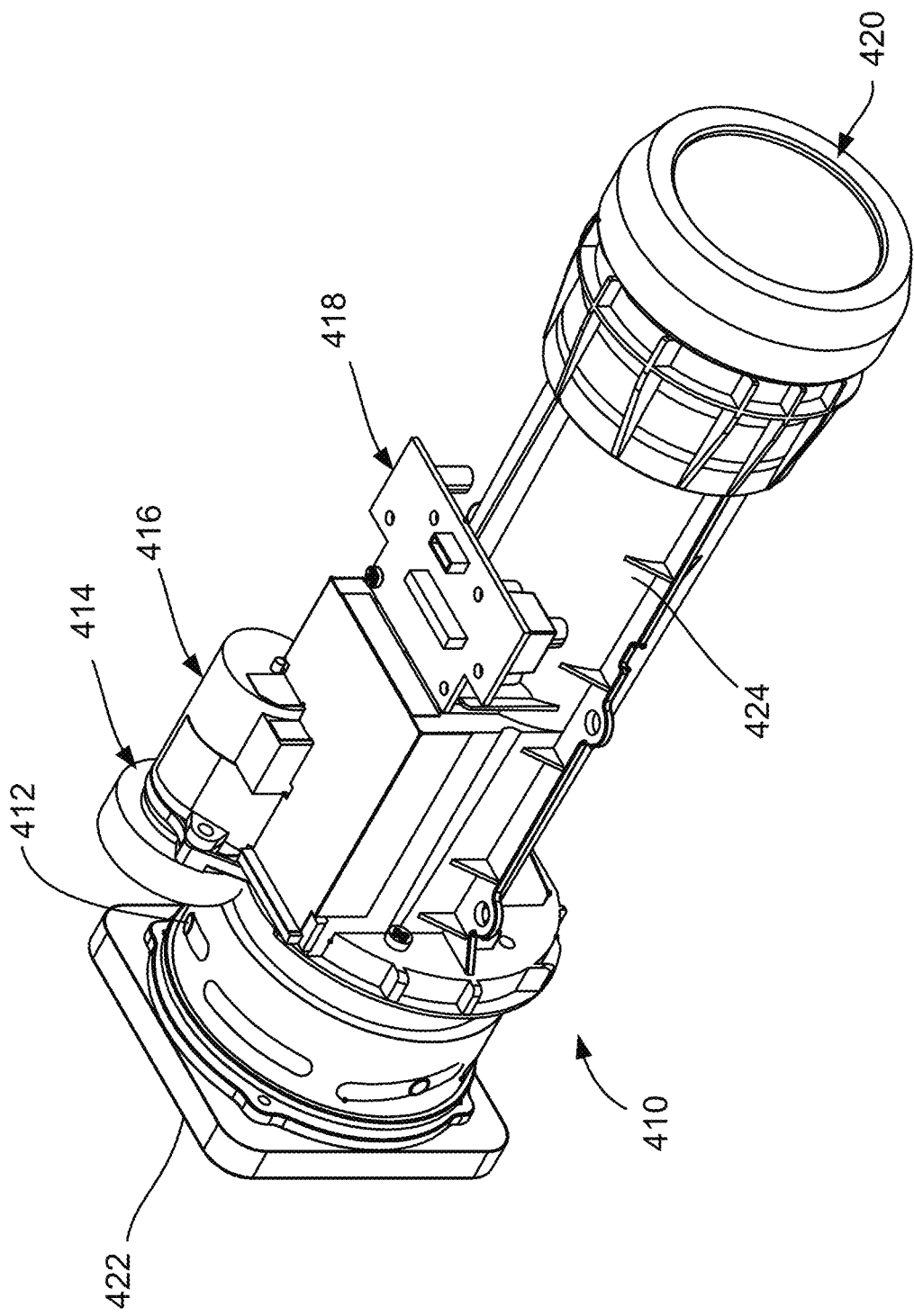
FIG. 15 shows example components of the optical lens module of FIG. 14.

As shown in FIG. 15, the optical lens module 410 is coupled by a mount 422 to the camera 104 to capture images of the fundus of the patient P's eyes. The optical lens module 410 includes an auto-focus mechanism 412, a gear train 414, and a motor 416. These components are controlled by an autofocus controller 418. The controller 418 is programmed to use the optical lens module 410 to automatically focus on the fundus of the patient P's eye once the fundus imaging system 102 is in position. At an opposite end of a barrel 424 of the optical lens module 410 is a lens 420.

As shown in FIGS. 16-22, the base assembly 450 allows for movement of the optical lens module 410 within the housing 200 along multiple axes to position the optical lens module 410 for imaging of the fundus. The base assembly 450 generally includes an x-base 452, a z-base 470, and a p-base 490.

Figure 16:
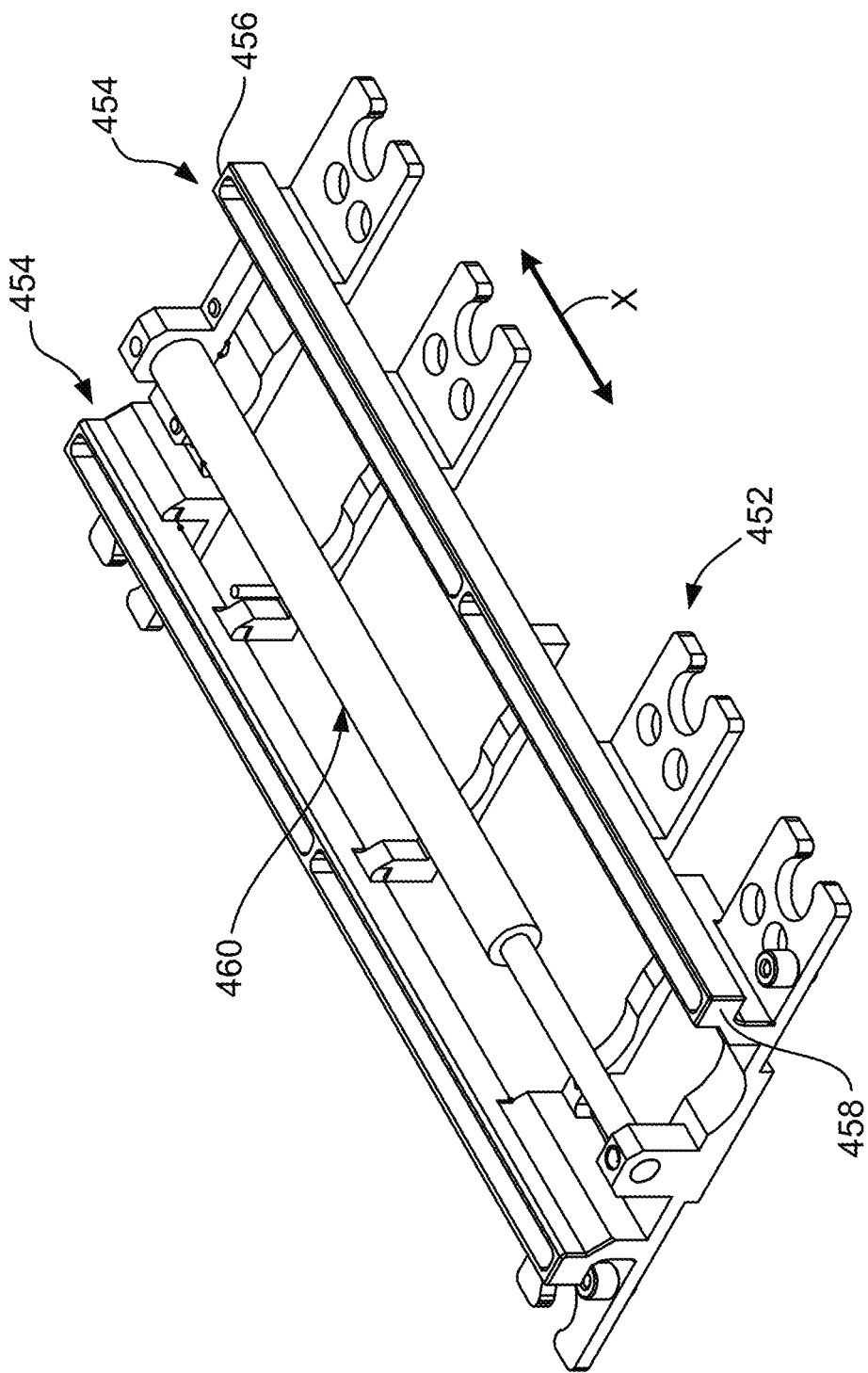
FIG. 16 shows example components of the optical lens module of FIG. 14.

As shown in FIG. 16, the x-base 452 allows for travel of the optical lens module 410 on railways 454 along an x-axis 466. This can include travel up to 78 mm on the railways 454 along the x-axis 466 from a first end 456 to a second end 458 of the x-base 452. A static lead screw 460 allows the z-base 470 to be driven along the lead screw 460 by a motor 472, as shown in FIGS. 17-18.

Figure 17:
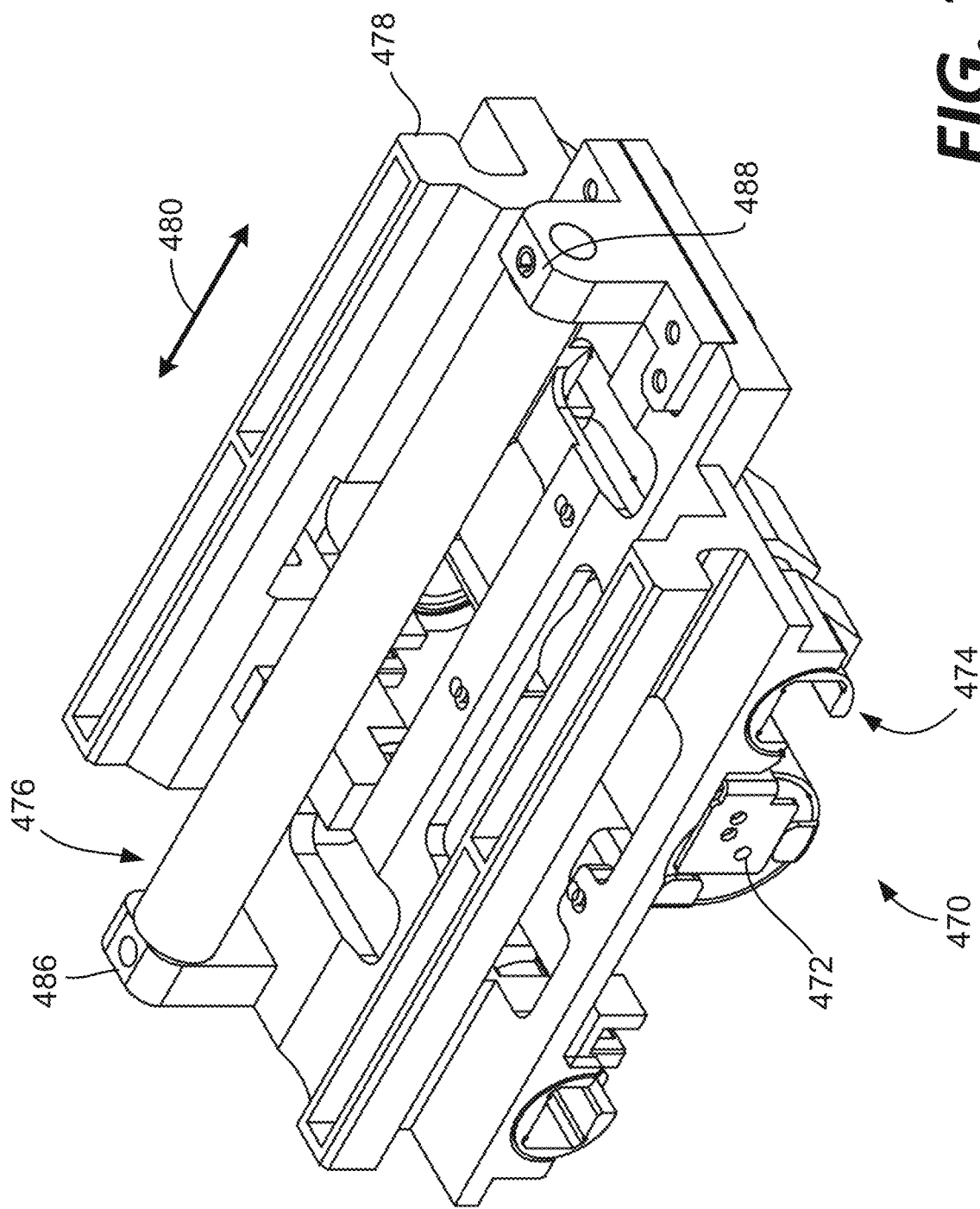
FIG. 17 shows example components of the optical lens module of FIG. 14.
Figure 18:
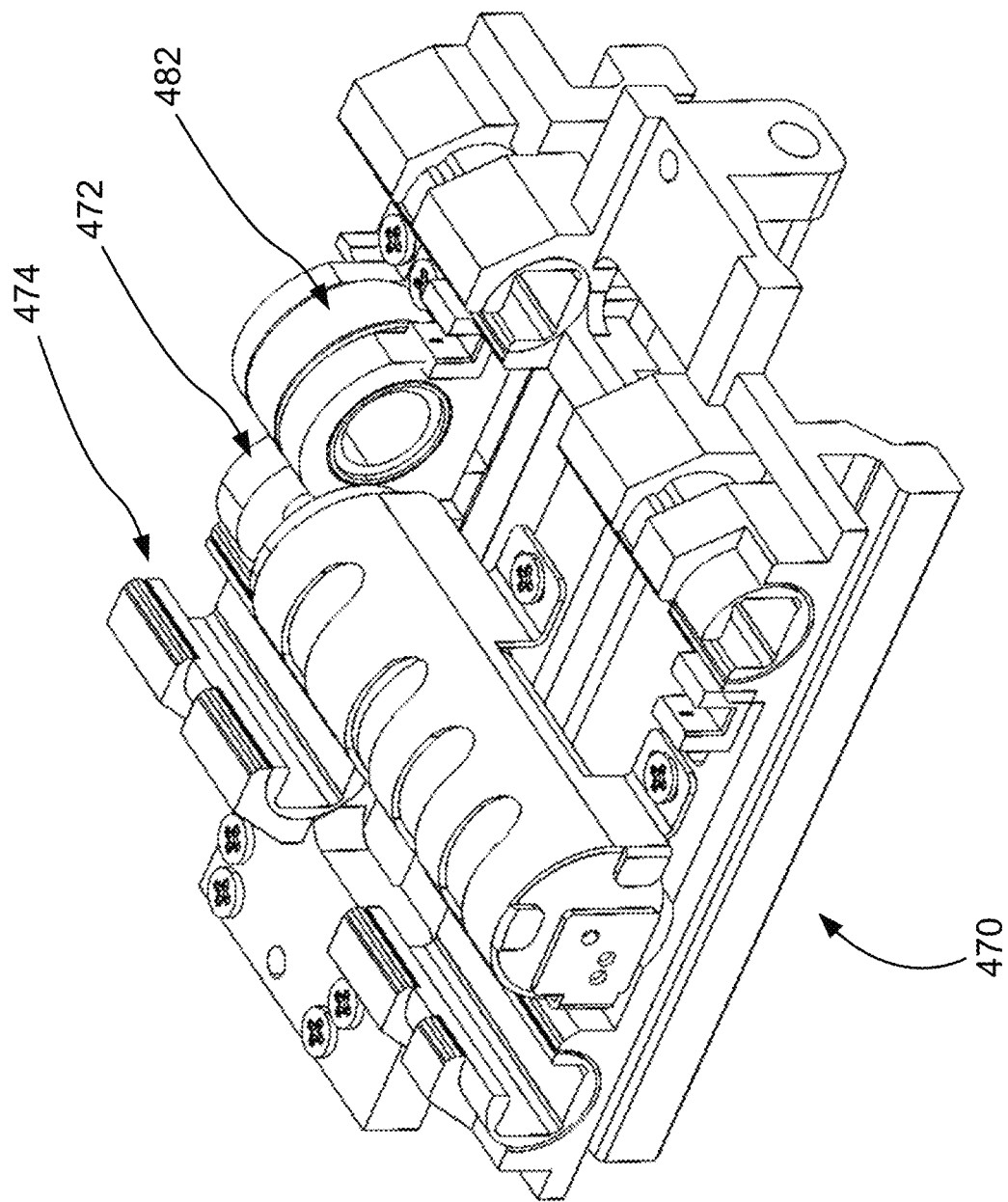
FIG. 18 shows example components of the optical lens module of FIG. 14.
Figure 19:
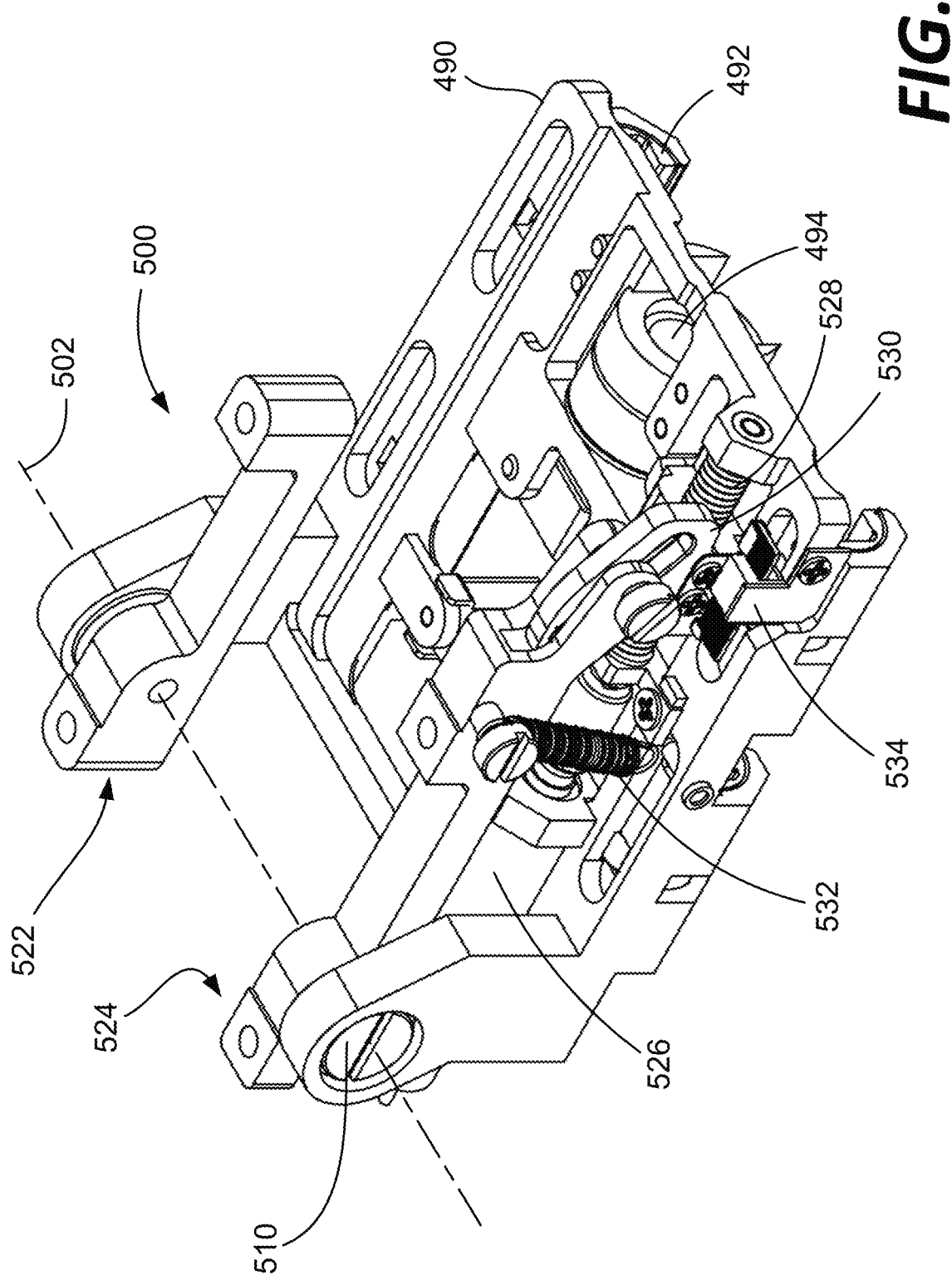
FIG. 19 shows example components of the optical lens module of FIG. 14.
Figure 20:
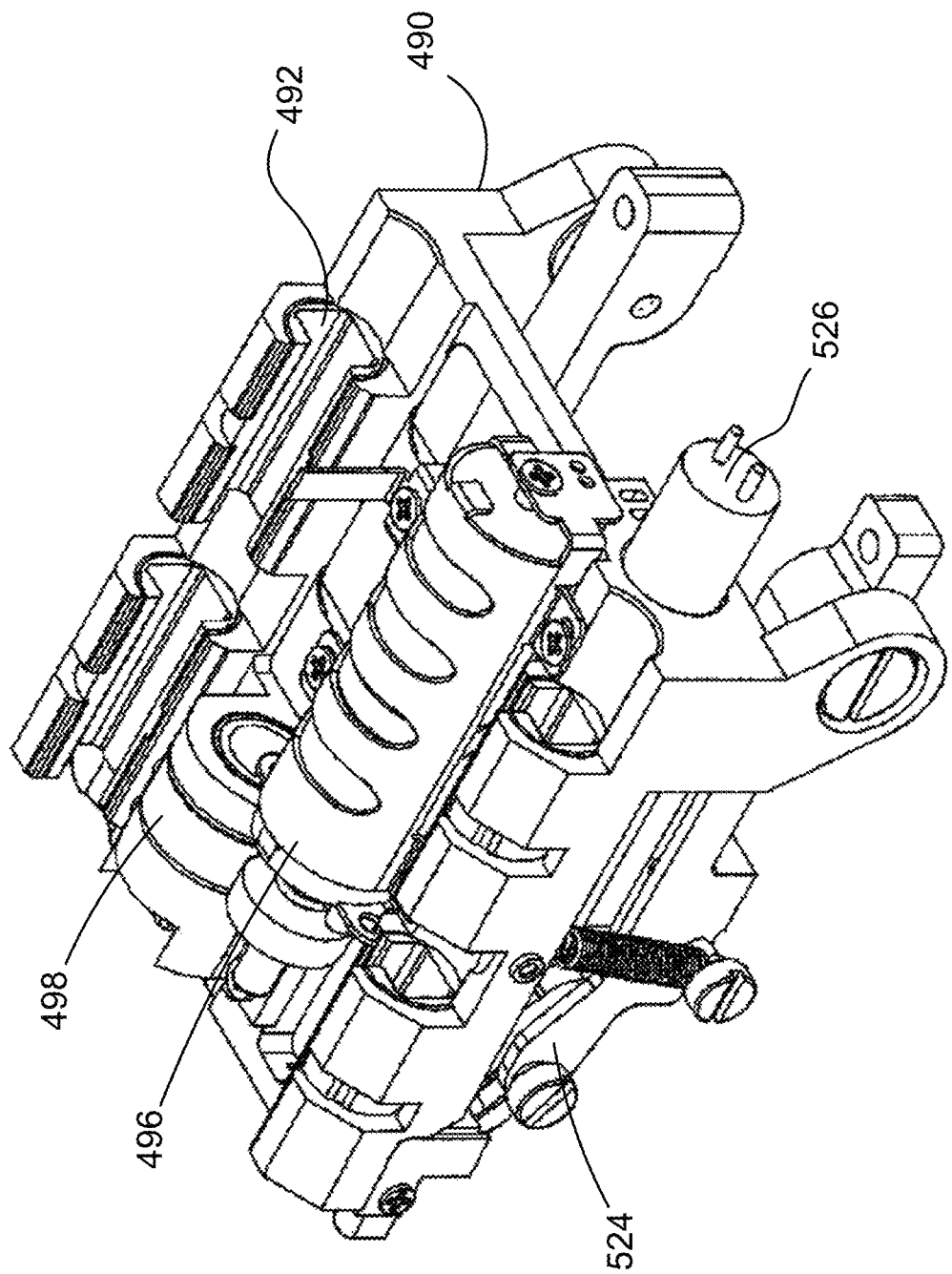
FIG. 20 shows example components of the optical lens module of FIG. 14.
Figure 21:
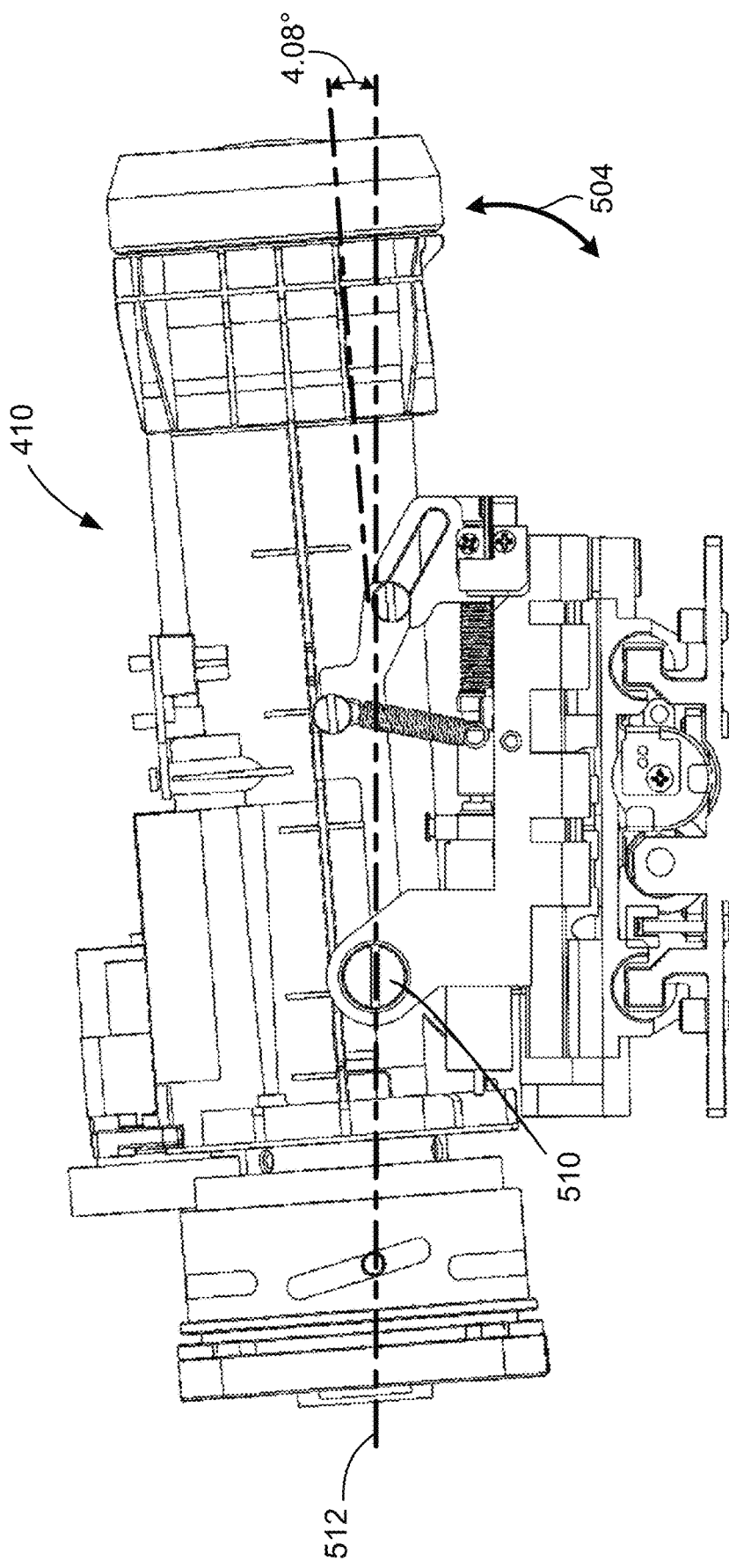
FIG. 21 shows example components of the optical lens module of FIG. 14.
Figure 22:
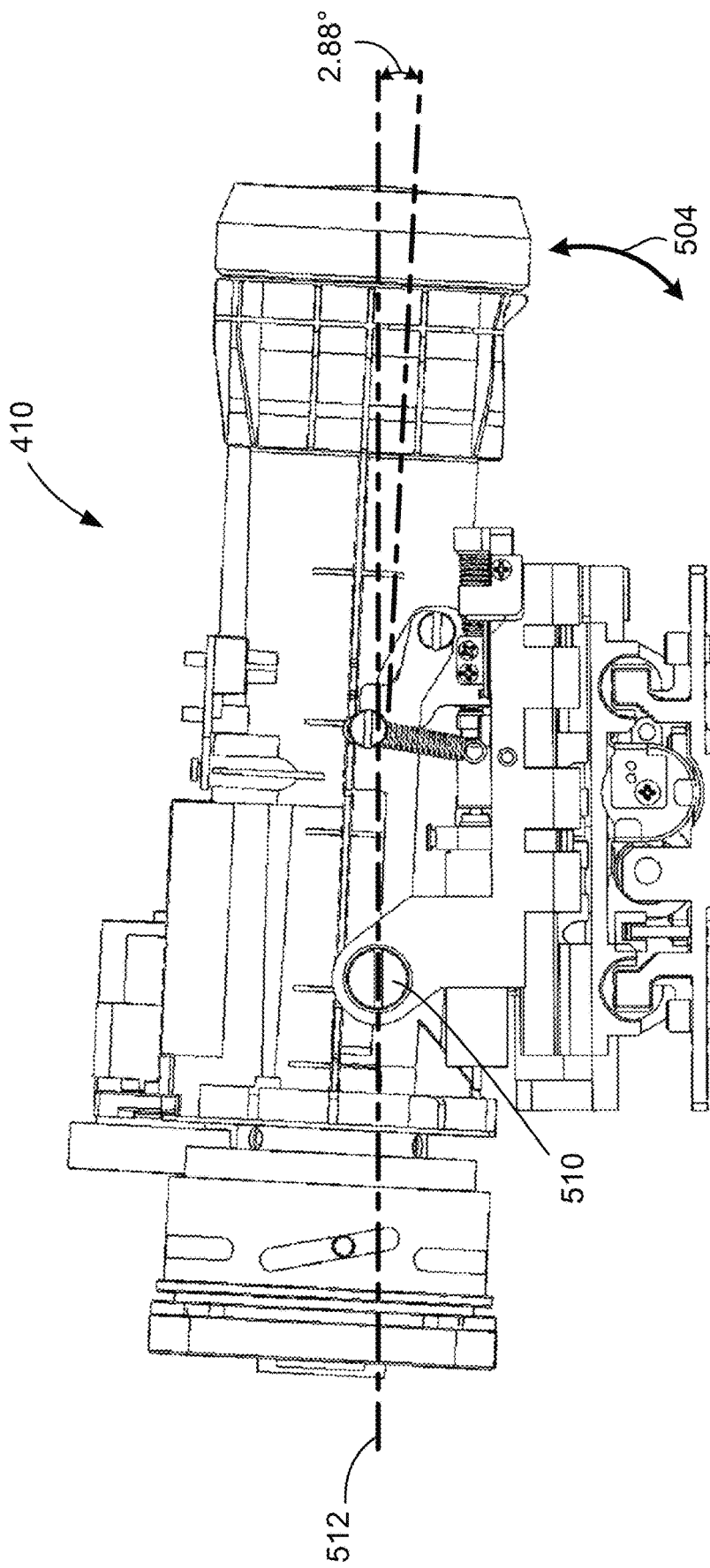
FIG. 22 shows example components of the optical lens module of FIG. 14.

Referring now to FIGS. 17-18, the z-base 470 includes bearings 474 that ride on the railways 454 of the x-base 452 to allow the z-base 470 to travel along the x-axis 466. A traveling nut 482 engages the lead screw 460 and is driven by the motor 472 to allow the z-base 470 to travel along the railways 454.

The z-base 470 includes a lead screw 476 that allows for travel of the optical lens module 410 along a z-axis 480 from a first end 486 to an opposite second end 488 of the lead screw 476. This can include travel up to 30 mm on railways 478 of the z-base 470 along the z-axis 480.

Referring now to FIGS. 19-22, the p-base 490 includes bearings 492 that ride on the railways 478 of the z-base 452 to allow the p-base 490 to travel along the z-axis 480. A traveling nut 498 engages the lead screw 476 and is driven by a motor 496 to allow the p-base 490 to travel along the railways 476 from the first end 486 to the second end 488 of the lead screw 476.

In this example, the fundus imaging system 102 also includes a y-pitch base 500 that allows the optical lens module 410 to be pitched in a y-pitch 504 about a bearing 510 along a y-axis 502. In this example, the pitch allows for 10.55 mm of travel, which results in +4.08 degrees (FIGS. 21) to −2.88 degrees (FIG. 22) of y-pitch 504 relative to a base axis of 512. Various other travels and pitches can be achieved as desired.

Support arms 522, 524 support the optical lens module 410 as the y-pitch base 500 pivots in the y-pitch 504. A motor 526 drives a nut 530 including a ramped surface along a lead screw 528 to create the pitch. A spring 532 biases the y-pitch base 500 into the level (0 degree) pitch position. An optical sensor 534 senses a position of the y-pitch base 500 relative to the A-base 490 to determine the specific pitch of the y-pitch base 500.

By providing movement along the x-axis 466 and the z-axis 480 (which is orthogonal to the x-axis 466), the optical lens module 410 can be moved into position within the housing 200 of the fundus imaging system 102 to image both eyes while the fundus imaging system 102 is placed against the head of the patient. Further, the optical lens module 410 can be pitched about the y-axis 502 to allow for fine movement of the optical lens module 410 that more closely tracks the generally movement of the eye. Moving the optical lens module 410 along three axes (i.e., three-axis actuator) allows for better imaging of the fundus without requiring the caregiver C or the patient P to physically move the fundus imaging system 102.

In some examples, the device is programmed to automatically move the camera into position along the three axes to capture the image. In such embodiments, the computing device 1800 is programmed to control the movement along the axes. Active eye tracking is used to position the camera relative to the eye. The system is programmed to monitor the infrared brightspot associated with a reflection of the cornea and automatically initiate capture of the image when the fundus is in the desired position relative to the camera. One example of such a system is described in U.S. patent application Ser. No. 15/009,988 filed on Jan. 29, 2016, the entirety of which is hereby incorporated by reference.

Figure 23:
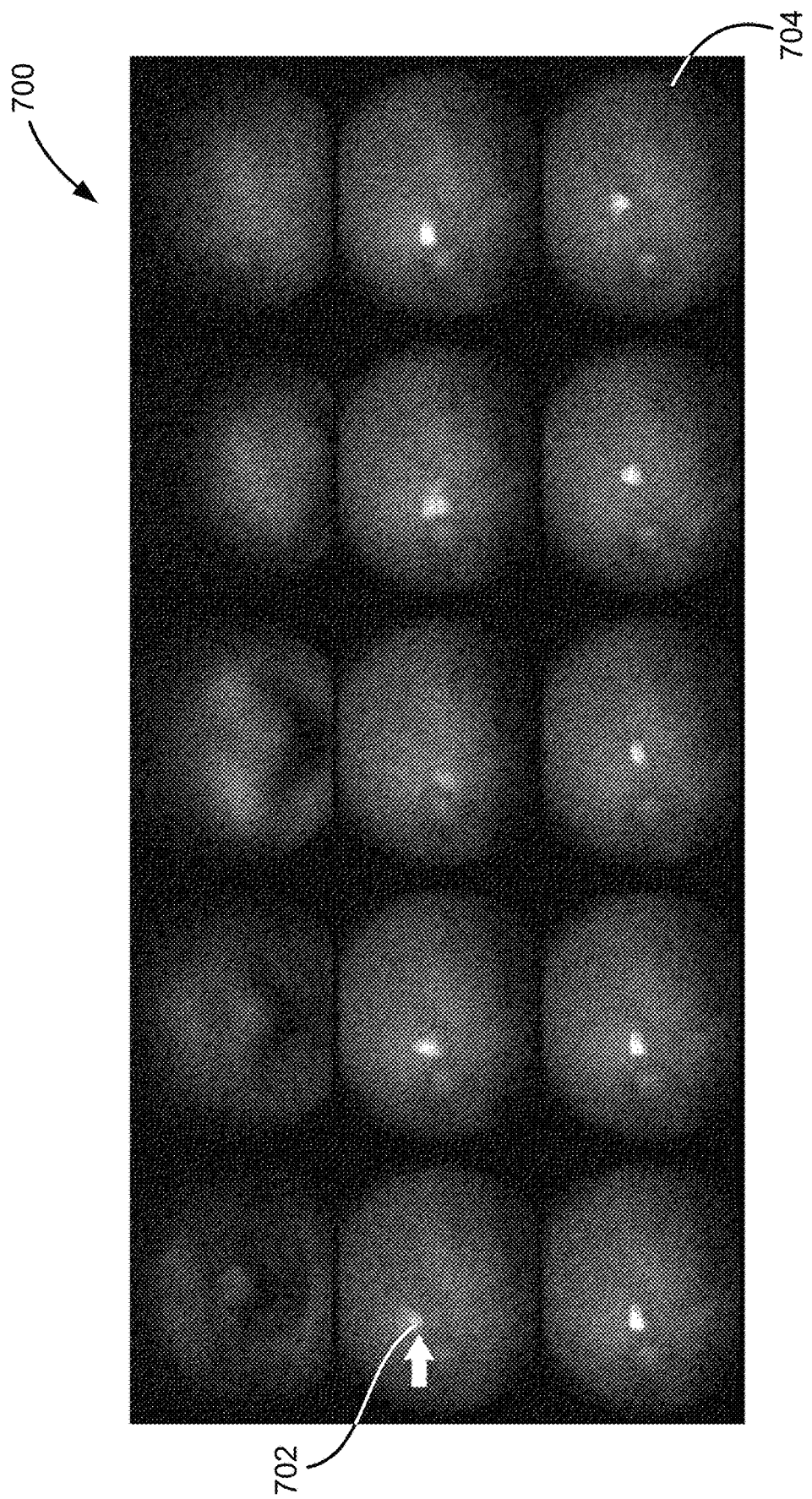
FIG. 23 shows a series of images depicting progression of the fundus imaging system of FIG. 2 into position for imaging.

For example, referring to FIG. 23, a series of images 700 depict a progression of the fundus imaging system 102 into position for imaging of the fundus. A brightspot 702, which is a reflection of light from a portion of the eye (i.e., the cornea), allows the fundus imaging system 102 to focus on the fundus for automatic imaging. The image or images are captured once the fundus imaging system 102 utilizes movement along the plurality of axes (x, y, z) to a position shown in image 704 for capture.

In manual configurations, the device is programmed to illustrate a target on the display of the device. The caregiver C can use controls on the display to move the camera along the axes to position the reflection from the cornea displayed on the display in the target. At that point, capture of the image can automatically be initiated. One example of such a system is described in U.S. patent application Ser. No. 15/054,558 filed on Feb. 26, 2016.

Figure 24:
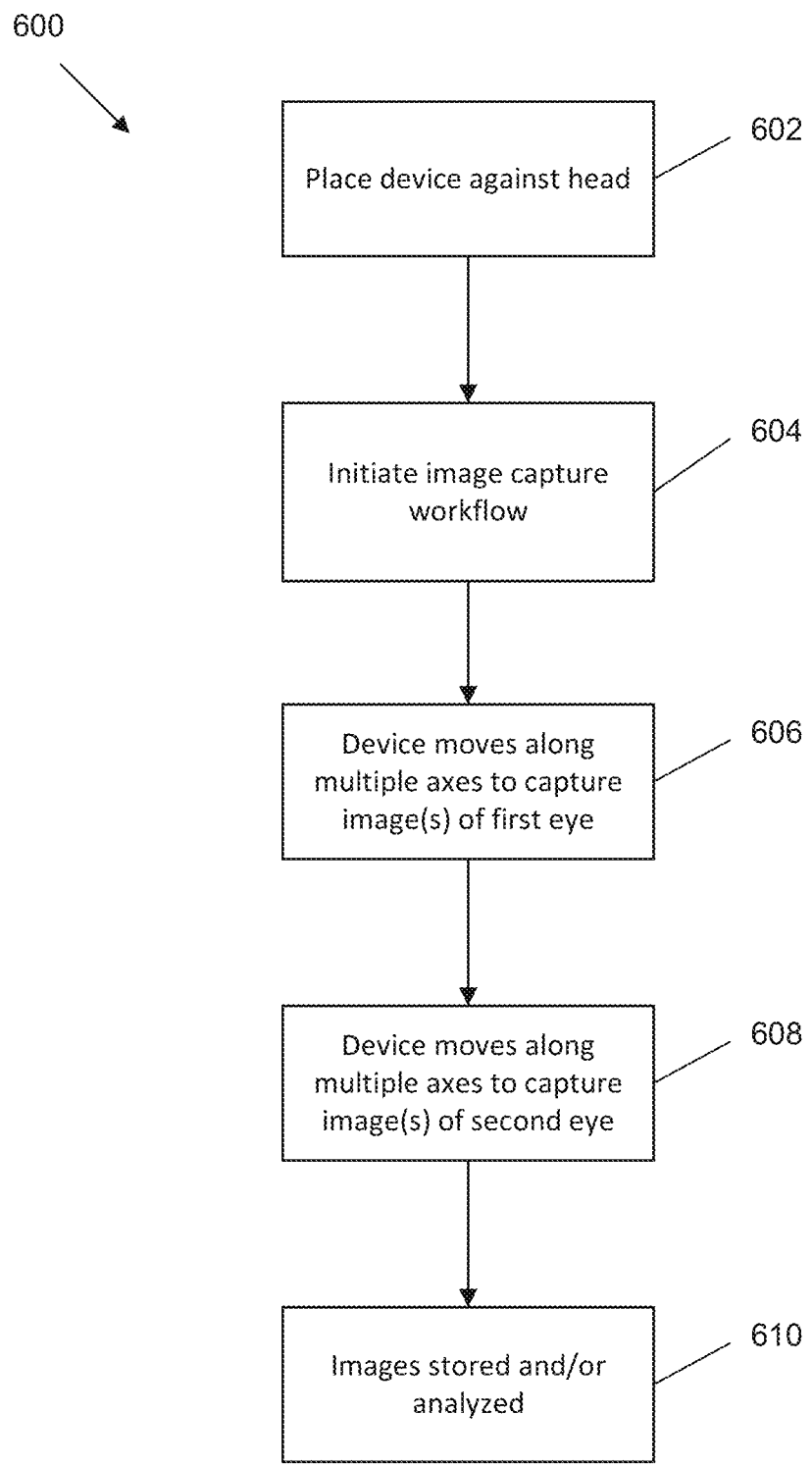
FIG. 24 is an example method of using the fundus imaging system of FIG. 2.

Referring now to FIG. 24, an example method 600 for capturing fundus images of the eyes is shown.

At operation 602, the handheld device 102 is placed over the eyes against the head of the patient P by the caregiver C (or the patient P can place the device). Next, at operation 604, the capture of the images is initiated. One example of such a workflow is provide in U.S. patent application Ser. No. 15/054,558 filed on Feb. 26, 2016. In one example, the caregiver C uses the display 108 to initiate the workflow for image capture. Alternatively, the workflow can be automatically initiated when the device 102 is placed against the patient P's head.

Next, at operation 606, the camera 104 is moved along three axes (x, y, z) to position the camera 104 to capture images of the first eye. In one example, the device is programmed to automatically move the camera along the axes into position to capture the image(s). In another embodiment, the device is programmed to allow the caregiver C to manually move the camera along the three axes (e.g., using controls shown in the display) to position the camera to capture the image(s).

Once the image(s) of the first eye are complete, control is passed to operation 608, and the camera 104 is moved along the x-axis within the device to be in position to capture images of the second eye. The camera 104 is thereupon moved along the three axes (x, y, z) to capture image(s) of the second eye. Again, this movement can be automatic or manual.

Finally, at operation 610, the images captured by the device 102 are stored and/or analyzed.

Figure 25:
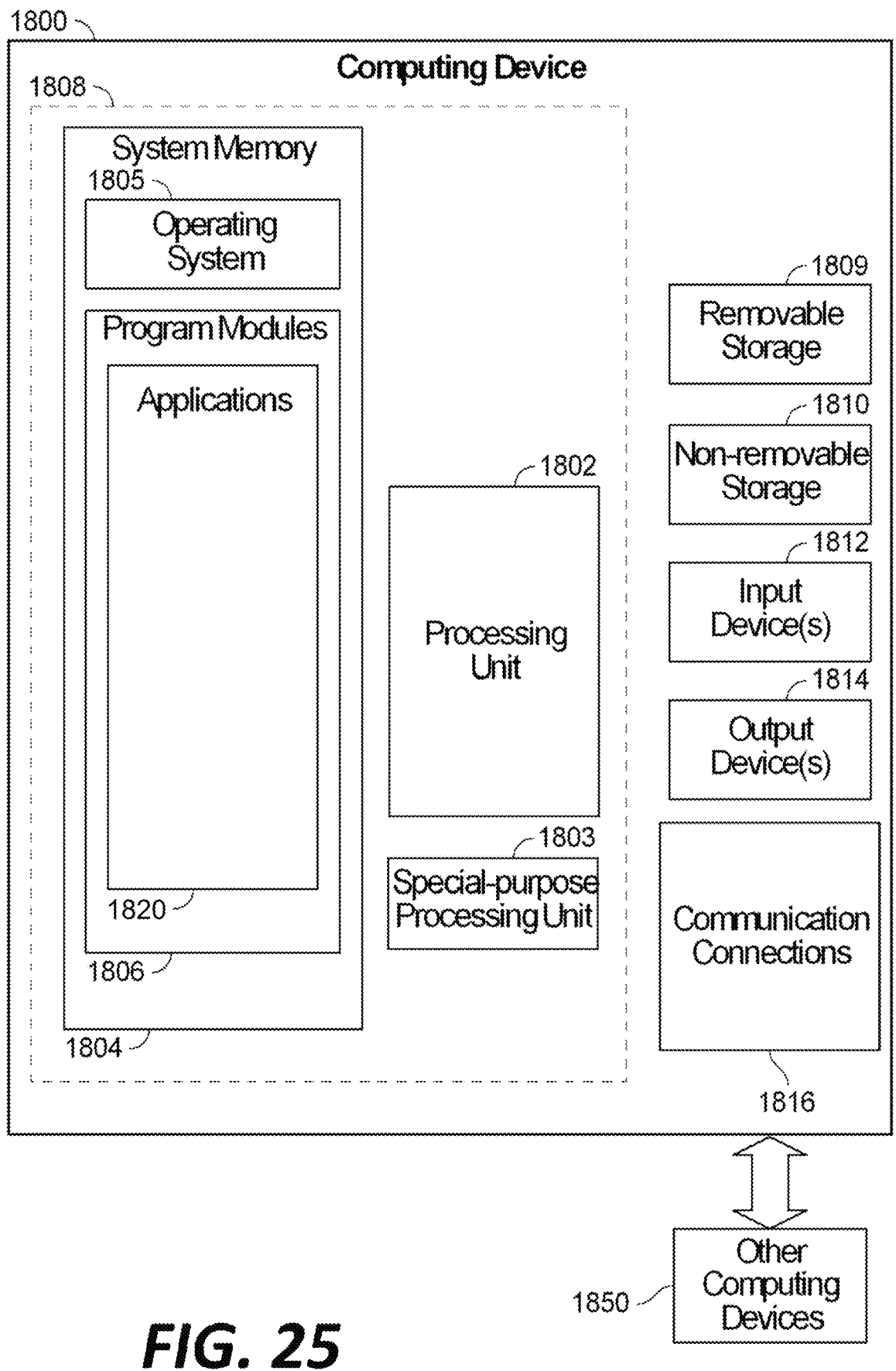
FIG. 25 is an example computing device used within the fundus imaging system of FIG. 2.

FIG. 25 is a block diagram illustrating physical components (i.e., hardware) of a computing device 1800 with which embodiments of the disclosure may be practiced. The computing device components described below may be suitable to act as the computing devices described above, such as wireless computing device and/or medical device of FIG. 1. In a basic configuration, the computing device 1800 may include at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820. The operating system 1805, for example, may be suitable for controlling the operation of the computing device 1800. Furthermore, embodiments of the disclosure may be practiced in conjunction with a graphics library, other operating systems, or any other application program and is not limited to any particular application or system. This basic configuration is illustrated in FIG. 25 by those components within a dashed line 1808. The computing device 1800 may have additional features or functionality. For example, the computing device 1800 may also include additional data storage devices (removable and/or non-removable) such as, for example, magnetic disks, optical disks, or tape. Such additional storage is illustrated by a removable storage device 1809 and a non-removable storage device 1810.

As stated above, a number of program modules and data files may be stored in the system memory 1804. While executing on the at least one processing unit 1802, the program modules 1806 may perform processes including, but not limited to, generate list of devices, broadcast user-friendly name, broadcast transmitter power, determine proximity of wireless computing device, connect with wireless computing device, transfer vital sign data to a patient's EMR, sort list of wireless computing devices within range, and other processes described with reference to the figures as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 25 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, may be operated via application-specific logic integrated with other components of the computing device 1800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1800 may also have one or more input device(s) 1812, such as a keyboard, a mouse, a pen, a sound or voice input device, a touch or swipe input device, etc. The output device(s) 1814 such as a display, speakers, a printer, etc. may also be included. The aforementioned devices are examples and others may be used. The computing device 1800 may include one or more communication connections 1816 allowing communications with other computing devices. Examples of suitable communication connections 1816 include, but are not limited to, RF transmitter, receiver, and/or transceiver circuitry; universal serial bus (USB), parallel, and/or serial ports.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates. These intermediary servers can be managed by the systems and methods described herein to update the maintenance requirements of the servers.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made.

The systems and method described herein result in a significant technical advantage. For example, the computing devices can be programmed to more efficiently capture fundus images. This allows the computing devices to accomplish an analysis of a greater number of images in a smaller amount of time.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A device for capturing an image of an eye, the device comprising:
   a housing having:
      a first end including a display; and
      a second end including a surface for surrounding first and second eyes;
   a camera positioned inside the housing, the camera including an optical lens module abutting a cavity on the second end of the housing, the cavity defined by the surface surrounding first and second eyes, the camera configured to capture the image of the eye;
   an optical sensor;
   at least one processing unit in communication with the camera; and
   a memory storing software instructions that, when executed by the at least one processing unit, cause the device to:
      move the optical lens module inside the cavity along a first axis, a second axis, and a third axis to align the optical lens module with the first eye;
      adjust a pitch of the optical lens module about a base axis inside the housing;

sense a position of a first base relative to a second base to determine the pitch of the optical lens module based on readings from the optical sensor; and capture the image of the first eye when the first eye is detected to be in a predetermined position relative to the optical lens module.

2. The device of claim 1, wherein the predetermined position is determined by a reflection of light from a portion of the first eye.

3. The device of claim 2, wherein the reflection of light is an infrared bright spot.

4. The device of claim 1, wherein the device is programmed to automatically move the optical lens module into the predetermined position.

5. The device of claim 4, wherein the device is programmed to use active eye tracking to automatically move the optical lens module along the first axis, the second axis, and the third axis.

6. The device of claim 1, wherein the device is programmed to allow manual movement of the optical lens module by illustrating a target on a display, and providing controls on the display for a user to move the optical lens module along the first axis, the second axis, and the third axis to position a reflection of light from a portion of the first eye inside the target.

7. The device of claim 1, further comprising at least one motor to move the optical lens module along the first axis, the second axis, and the third axis.

8. The device of claim 1, wherein the memory stores further instructions which, when executed by the at least one processing unit, cause the device to:

move the optical lens module inside the cavity along the first axis, the second axis, and the third axis to align the optical lens module with the second eye; and capture another image of the second eye when the second eye is detected to be in the predetermined position relative to the optical lens module.

9. The device of claim 1, wherein the housing is sized to be handheld.

10. A method for capturing an image of an eye, the method comprising:

moving an optical lens module relative to a cavity defined by a surface surrounding first and second eyes, the optical lens module being moved along a first axis, a second axis, and a third axis relative to the cavity to align the optical lens module with the first eye;

adjusting a pitch of the optical lens module about a base axis inside a housing;

sensing a position of a first base relative to a second base to determine the pitch of the optical lens module;

capturing the image of the first eye when the first eye is detected to be in a predetermined position relative to the optical lens module;

moving the optical lens module along the first axis, the second axis, and the third axis relative to the cavity to align the optical lens module with the second eye; and capturing another image of the second eye when the second eye is detected to be in the predetermined position relative to the optical lens module.

11. The method of claim 10, wherein the predetermined position is determined by a reflection of light from a portion of the first eye.

12. The method of claim 11, wherein the reflection of light is an infrared bright spot.

13. The method of claim 10, wherein moving the optical lens module along the first axis, the second axis, and the third axis is performed without physically moving the housing in which the optical lens module is positioned.

14. The method of claim 13, wherein the housing is sized to be handheld.

15. A non-transitory computer readable storage media storing data instructions, which when executed by a computing device, cause the computing device to:

move an optical lens module relative to a cavity defined by a surface surrounding first and second eyes, the optical lens module being moved along a first axis, a second axis, and a third axis relative to the cavity to align the optical lens module with the first eye;

adjust a pitch of the optical lens module about a base axis inside a housing;

sense a position of a first base relative to a second base to determine the pitch of the optical lens module;

capture an image of the first eye when the first eye is detected to be in a predetermined position relative to the optical lens module;

move the optical lens module along the first axis, the second axis, and the third axis relative to the cavity to align the optical lens module with the second eye; and capture another image of the second eye when the second eye is detected to be in the predetermined position relative to the optical lens module.

16. The non-transitory computer readable storage media of claim 15, wherein the predetermined position is determined by a reflection of light from a portion of the first eye.

17. The non-transitory computer readable storage media of claim 16, wherein the reflection of light is an infrared bright spot.

18. The non-transitory computer readable storage media of claim 15, wherein the optical lens module is moved along the first axis, the second axis, and the third axis without physically moving the housing in which the optical lens module is positioned.

19. The non-transitory computer readable storage media of claim 18, wherein the housing is sized to be handheld.

* * * * *